(12) United States Patent
Hefner et al.

(10) Patent No.: US 11,072,820 B2
(45) Date of Patent: Jul. 27, 2021

(54) DIGITAL AMPLIFICATION ASSAYS WITH UNCONVENTIONAL AND/OR INVERSE CHANGES IN PHOTOLUMINESCENCE

(71) Applicant: Bio-Rad Laboratories, Inc., Hercules, CA (US)

(72) Inventors: Eli A. Hefner, Fairfield, CA (US); Dianna Maar, Mountain House, CA (US)

(73) Assignee: Bio-Rad Laboratories, Inc., Hercules, CA (US)

( * ) Notice: Subject to any disclaimer, the term of this patent is extended or adjusted under 35 U.S.C. 154(b) by 158 days.

(21) Appl. No.: 16/159,488

(22) Filed: Oct. 12, 2018

(65) Prior Publication Data

US 2019/0119736 A1    Apr. 25, 2019

Related U.S. Application Data

(60) Provisional application No. 62/574,694, filed on Oct. 19, 2017.

(51) Int. Cl.
| | | |
|---|---|---|
| *C12Q 1/6844* | (2018.01) | |
| *C12Q 1/6816* | (2018.01) | |
| *G01N 21/64* | (2006.01) | |

(52) U.S. Cl.
CPC ......... *C12Q 1/6844* (2013.01); *C12Q 1/6816* (2013.01); *G01N 21/6428* (2013.01); *G01N 2021/6432* (2013.01)

(58) Field of Classification Search
CPC .............................. C12Q 1/6844; C12Q 1/6816
See application file for complete search history.

(56) References Cited

U.S. PATENT DOCUMENTS

| | | |
|---|---|---|
| 5,304,810 A | 4/1994 | Amos |
| 6,020,141 A | 2/2000 | Pantoliano et al. |
| 6,379,888 B1 | 4/2002 | Nadeau et al. |
| 7,801,226 B2 | 9/2010 | Suh et al. |
| 8,148,515 B1 | 4/2012 | Mao et al. |
| 8,951,939 B2 | 2/2015 | Saxonov et al. |
| 9,156,010 B2 | 10/2015 | Colston, Jr. et al. |
| 9,217,175 B2 | 12/2015 | Regan et al. |
| 9,222,128 B2 | 12/2015 | Saxonov et al. |
| 9,458,511 B2 | 10/2016 | Koehler et al. |
| 9,523,116 B2 | 12/2016 | Tzonev et al. |
| 9,702,822 B2 | 7/2017 | Litterst et al. |
| 2005/0266448 A1 | 12/2005 | Hagiwara et al. |
| 2006/0078888 A1 | 4/2006 | Griffiths et al. |
| 2009/0069194 A1 | 3/2009 | Ramakrishnan |
| 2009/0239308 A1 | 9/2009 | Dube et al. |
| 2009/0311713 A1 | 12/2009 | Pollack et al. |
| 2010/0022414 A1 | 1/2010 | Link et al. |
| 2010/0092973 A1 | 4/2010 | Davies et al. |
| 2010/0173394 A1 | 7/2010 | Colston, Jr. et al. |
| 2010/0233686 A1 | 9/2010 | Higuchi et al. |
| 2010/0248385 A1 | 9/2010 | Tan et al. |
| 2010/0304978 A1 | 12/2010 | Deng et al. |
| 2011/0000560 A1 | 1/2011 | Miller et al. |
| 2011/0104686 A1 | 5/2011 | Litterst et al. |
| 2011/0159499 A1 | 6/2011 | Hindson et al. |
| 2011/0244455 A1 | 10/2011 | Larson et al. |
| 2011/0250597 A1 | 10/2011 | Larson et al. |
| 2012/0122714 A1 | 5/2012 | Samuels et al. |
| 2012/0164690 A1 | 6/2012 | Wang |
| 2012/0208241 A1 | 8/2012 | Link |
| 2012/0219947 A1 | 8/2012 | Yurkovetsky et al. |
| 2012/0220494 A1 | 8/2012 | Samuels et al. |
| 2012/0252015 A1 | 10/2012 | Hindson et al. |
| 2012/0264646 A1 | 10/2012 | Link et al. |
| 2012/0302448 A1 | 11/2012 | Hutchison et al. |

(Continued)

FOREIGN PATENT DOCUMENTS

| | | |
|---|---|---|
| AU | 2012129187 A1 | 9/2012 |
| EP | 1087020 A2 | 3/2001 |

(Continued)

OTHER PUBLICATIONS

Wadle, Real-time PCR probe optimization using design experiments approach, Biomol. Detec. Quantif., 7:1-8, Mar. 2016. (Year: 2016).*

Arya, Manit et al., "Basic principles of real-time quantitative PCR", Expert Review of Molecular Diagnostics, vol. 5, No. 2, (2005), 11 pages.

Beer, N. Reginald et al., "On-Chip, Real-Time, Single-Copy Polymerase Chain Reaction in Picoliter Droplets", Analytical Chemistry, vol. 79, No. 22, Nov. 15, 2007, pp. 8471-8475.

Bhagwat, Arvind A., "Simultaneous detection of *Escherichia coli* O157:H7, *Listeria monocytogenes* and *Salmonella* strains by real-time PCR", International Journal of Food Microbiology, vol. 84, (2003), pp. 217-224.

Butler, John M., "Capillary electrophoresis as a tool for optimization of multiplex PCR reactions", Fresenius J Analytical Chemistry, vol. 369, (2001), pp. 200-205.

(Continued)

*Primary Examiner* — Angela M. Bertagna
*Assistant Examiner* — Carolyn L Greene
(74) *Attorney, Agent, or Firm* — Kolisch Hartwell, P.C.

(57) ABSTRACT

Methods of, and compositions for, analysis using digital amplification assays with unconventional/inverse changes in photoluminescence to indicate the presence of one or more targets. In an exemplary method, isolated volumes may be formed, only a subset of which contain a target. Each volume may include a probe having a label, a sink having a quencher and configured to hybridize with the probe to quench the label, and a separator configured to hybridize with the probe and/or the sink to block hybridization of the sink with the probe. An amplification reaction may be performed in the volumes to generate an amplicon corresponding to the target. The separator may hybridize with the amplicon, and may be extended or degraded by the amplification reaction. Photoluminescence of the label may be detected from the volumes, and the photoluminescence of target-positive volumes may be less than that of target-negative volumes.

19 Claims, 11 Drawing Sheets

(56) References Cited

U.S. PATENT DOCUMENTS

| | | |
|---|---|---|
| 2012/0309002 A1 | 12/2012 | Link |
| 2012/0316074 A1 | 12/2012 | Saxonov |
| 2012/0322058 A1 | 12/2012 | Regan et al. |
| 2012/0329664 A1 | 12/2012 | Saxonov et al. |
| 2013/0017968 A1 | 1/2013 | Gurtner et al. |
| 2013/0040841 A1 | 2/2013 | Saxonov et al. |
| 2013/0059754 A1 | 3/2013 | Tzonev |
| 2013/0178378 A1 | 7/2013 | Hatch et al. |
| 2014/0057273 A1 | 2/2014 | Litterst et al. |
| 2014/0171341 A1 | 6/2014 | Jouvenot et al. |
| 2014/0221237 A1 | 8/2014 | Tzonev et al. |
| 2014/0221238 A1 | 8/2014 | Regan et al. |
| 2014/0274799 A1 | 9/2014 | Koehler et al. |
| 2015/0148250 A1 | 5/2015 | Regan et al. |
| 2015/0307919 A1 | 10/2015 | Ness et al. |
| 2016/0265041 A1 | 9/2016 | Maar et al. |
| 2017/0166957 A1 | 6/2017 | Regan et al. |

FOREIGN PATENT DOCUMENTS

| | | |
|---|---|---|
| EP | 1087020 A3 | 7/2003 |
| WO | 03064691 A2 | 8/2003 |
| WO | 2006002167 A2 | 1/2006 |
| WO | 2008074023 A2 | 6/2008 |
| WO | 2008074023 A3 | 6/2008 |
| WO | 2010018465 A2 | 2/2010 |
| WO | 2010036352 A1 | 4/2010 |
| WO | 2011100604 A2 | 8/2011 |
| WO | 2011143478 A2 | 11/2011 |
| WO | 2012129187 A1 | 9/2012 |
| WO | 2014031908 A1 | 2/2014 |
| WO | 2014121239 A2 | 8/2014 |
| WO | 2014121240 A1 | 8/2014 |

OTHER PUBLICATIONS

Cawthon, Richard M., "Telomere measurement by quantitative PCR", Nucleic Acids Research, vol. 30, No. 10, (2002), pp. 1-6.

Dube, Simant et al., "Mathematical Analysis of Copy Number Variation in a DNA Sample Using Digital PCR on a Nanofluidic Device", PLoS One, vol. 3, Issue 8, Aug. 2008, pp. 1-9.

Higuchi, Russell et al., "Simultaneous Amplification and Detection of Specific DNA Sequences", Biotechnology, vol. 10, Apr. 1992, pp. 413-417.

Higuchi, Russell et al., "Kinetic PCR Analysis: Real-time Monitoring of DNA Amplification Reactions", Biotechnology, vol. 11, Sep. 11, 1993, pp. 1026-1030.

Hindson, Benjamin J. et al., "High-Throughput Droplet Digital PCR System for Absolute Quantitation of DNA Copy Number", Analytical Chemistry, vol. 83, Oct. 28, 2011, pp. 8604-8610.

Hua, Zhishan et al., "Multiplexed Real-Time Polymerase Chain Reaction on a Digital Microfluidic Platform" Analytical Chemistry, vol. 82, No. 6, Mar. 15, 2010, pp. 2310-2316.

Kiss, Margaret Macris et al., "High-Throughput Quantitative Polymerase Chain Reaction in Picoliter Droplets", Analytical Chemistry, vol. 80, No. 23, Dec. 1, 2008, pp. 8975-8981.

Lind, Kristina et al., "Combining sequence-specific probes and DNA binding dyes in real-time PCR for specific nucleic acid quantification and melting curve analysis", Biotechniques, vol. 40, No. 3, Mar. 2006, pp. 315-319.

Mao, Fei et al., "Characterization of EvaGreen and the implication of its physicochemical properties for qPCR applications", BMC Technology, vol. 7, No. 76, Nov. 9, 2007, pp. 1-16.

Markey, Amelia L. et al., "High-throughput droplet PCR", Methods, vol. 50, Feb. 2, 2010, pp. 277-281.

Martin, Kendall J. et al., "Fungal-specific PCR primers developed for analysis of the ITS region of environmental DNA extracts", BMC Microbiology, vol. 5, No. 28, May 18, 2005, pp. 1-11.

McDermott, Geoffrey P. et al., "Multiplexed Target Detection Using DNA-Binding Dye Chemistry in Droplet Digital PCR", Analytical Chemistry, vol. 85, Nov. 3, 2013, pp. 11619-11627.

Nakano, Michihiko et al., "Single-molecule PCR using water-in-oil emulsion", Journal of Biotechnology, vol. 102, pp. 117-124, Jan. 17, 2003.

Ottesen, Elizabeth A. et al., "Microfluidic Digital PCR Enables Multigene Analysis of Individual Environmental Bacteria", Science, vol. 314, Dec. 1, 2006, pp. 1464-1467.

Pekin, Deniz, "Quantitative and Sensitive Detection of Rare Mutations Using Droplet-Based Microfluidics", Lab Chip, vol. 11, (2011), pp. 2156-2166.

Pinheiro, Leonardo B. et al., "Evaluation of a Droplet Digital Polymerase Chain Reaction Format for DNA Copy Number Quantification", Analytical Chemistry, vol. 84, Nov. 28, 2011, pp. 1003-1011.

Pohl, Gudrun et al., "Principle and applications of digital PCR", Expert Review of Molecular Diagnostics, vol. 4, No. 1 (2004) pp. 41-47.

Qin, Jian et al., "Studying copy number variations using a nanofluidic platform", Nucleic Acids Research, vol. 36, No. 18, Aug. 18, 2008, pp. 1-8.

Schaerli, Yolanda et al., "The potential of microfluidic water-in-oil droplets in experimental biology", Molecular BioSystems, vol. 5, Oct. 12, 2009, pp. 1392-1404.

Therianos, Stavros et al., "Single-Channel Quantitative Multiplex Reverse Transcriptase-Polymerase Chain Reaction for Large Numbers for Gene Products Differentiates Nondemented from Neuropathological Alzheimer's Disease", American Journal of Pathology, vol. 164, No. 3, Mar. 2004, pp. 795-806.

Todorov, Tihomir et al,. "A Unified Rapid PCR Method for Detection of Normal and Expanded Trinucleotide Alleles of CAG Repeats in Huntington Chorea and CGG Repeats and Fragile X Syndrome", Molecular Biotechnology, Vo. 45, Mar. 9, 2010, pp. 150-154.

Vogelstein, Bert et al., "Digital PCR", Proceedings of the National Academy of Science USA, vol. 96, Aug. 1999, Genetics, pp. 9236-9241.

Wang, Weijie et al., "DNA quantification using EvaGreen and a real-time PCR instrument", Analytical Biochemistry, vol. 356, Jun. 9, 2006, pp. 303-305.

Wu, Yajun et al., "Detection of olive oil using the Evagreen real-time PCR method", European Food Research and Technology, vol. 227, Feb. 13, 2008, pp. 1117-1124.

Ye, Shu et al., "An efficient procedure for genotyping single nucleotide polymorphisms", Nucleic Acids Research, vol. 29, No. 17, (2001), pp. 1-8.

Zhong, Qun, "Multiplex digital PCR: breaking the one target per color barrier of quantitative PCR", Lab Chip, vol. 11, (2011), pp. 2167-2174.

Zimmerman, Bernhard G. et al., "Digital PCR: a powerful new tool for noninvasive prenatal diagnosis?", Prenatal Diagnosis, vol. 28, Nov. 10, 2008, pp. 1087-1093.

Ullrich, Thomas et al., "Competitive Reporter Monitored Amplification (CMA)—Quantification of Molecular Targets by Real Time Monitoring of Competitive Reporter Hybridization", PLOS One, vol. 7, Issue 4, Apr. 2012, 13 pages.

Young, Lee W., Authorized Officer, ISA/US, Commissioner for Patents, "International Search Report" in connection with related International Application No. PCT/US2018/055718, dated Dec. 27, 2018, 2 pages.

Young, Lee W., Authorized Officer, ISA/US, Commissioner for Patents, "Written Opinion of the International Searching Authority" in connection with related International Application No. PCT/US2018/055718, dated Dec. 27, 2018, 6 pages.

Lievens, A., et al. "Measuring Digital PCR Quality: Performance Parameters and Their Optimization." PloS one 11.5 (published May 5, 2016): e0153317, 21 pages.

European Patent Office, Extended European Search Report in European Patent Application No. 18869286.7-1111 (dated May 11, 2021), 6 pages.

\* cited by examiner

DIGITAL AMPLIFICATION ASSAYS WITH UNCONVENTIONAL AND/OR INVERSE CHANGES IN PHOTOLUMINESCENCE

CROSS-REFERENCE TO PRIORITY APPLICATION

This application is based upon and claims the benefit under 35 U.S.C. § 119(e) of U.S. Provisional Patent Application Ser. No. 62/574,694, filed Oct. 19, 2017, which is incorporated herein by reference in its entirety for all purposes.

CROSS-REFERENCES TO OTHER MATERIALS

This application incorporates by reference in their entireties for all purposes the following materials: U.S. Pat. No. 7,041,481, issued May 9, 2006; U.S. Patent Application Publication No. 2010/0173394 A1, published Jul. 8, 2010; U.S. Patent Application Publication No. 2012/0322058 A1, published Dec. 20, 2012; U.S. Patent Application Publication No. 2013/0040841 A1, published Feb. 14, 2013; U.S. Patent Application Publication No. 2015/0148250 A1, published May 28, 2015; and Joseph R. Lakowicz, PRINCIPLES OF FLUORESCENCE SPECTROSCOPY ($2^{nd}$ Ed. 1999).

INTRODUCTION

Digital amplification assays can quantify a nucleic acid target (a target sequence) in a sample. In a typical digital assay, the sample is divided into a set of isolated volumes, such as droplets, at partial occupancy of the target. Copies of the target are stochastically present in the volumes, with only a subset of the volumes containing at least one copy of the target. Each of the volumes is formulated to contain the same set of amplification reagents for target-dependent generation of a product through an amplification reaction, such as PCR. A probe having a fluorescent label also is included in each of the volumes to indicate whether or not the target-dependent amplification reaction has occurred in each individual volume. After performing the reaction, such as by thermally cycling the volumes, the fluorescence of the label in each volume can be detected. Individual volumes are then classified as positive or negative for the target based on the intensity of the fluorescence. The concentration of the target in the sample then can be calculated through Poisson statistics based on the number of volumes that are positive (or that are negative) for the target and the total number of volumes (positive and negative for the target).

Multiplex digital assays can quantify two or more different targets with the same set of volumes. Each of the volumes may contain target-specific probes, with each probe corresponding to a different target and having a spectrally distinguishable label. The level of target multiplexing can be increased further by using the same fluorescent label to report amplification of two or more different targets at distinguishable characteristic intensities of fluorescence. For example, volumes positive for a first target may exhibit a smaller increase in the fluorescence intensity of the label over target-negative volumes, while volumes positive for a second target may exhibit a larger increase in the fluorescence intensity. However, a disadvantage of this intensity-based multiplexing is that the characteristic intensities for different targets can be dependent upon assay conditions, and thus can shift somewhat relative to one another each time the assay is performed. These shifts can make the assay less robust and accurate.

A new approach for performing multiplex digital assays with more options for adjusting fluorescence intensities is needed.

SUMMARY

The present disclosure provides methods of, and compositions for, analysis using digital amplification assays with unconventional/inverse changes in photoluminescence to indicate the presence of one or more targets. In an exemplary method, isolated volumes may be formed, only a subset of which contain a target. Each volume may include a probe having a label, a sink having a quencher and configured to hybridize with the probe to quench the label, and a separator configured to hybridize with the probe and/or the sink to block hybridization of the sink with the probe. An amplification reaction may be performed in the volumes to generate an amplicon corresponding to the target. The separator may hybridize with the amplicon, and may be extended or degraded by the amplification reaction. Photoluminescence of the label may be detected from the volumes, and the photoluminescence of target-positive volumes may be less than that of target-negative volumes.

DETAILED DESCRIPTION

Figure 1:
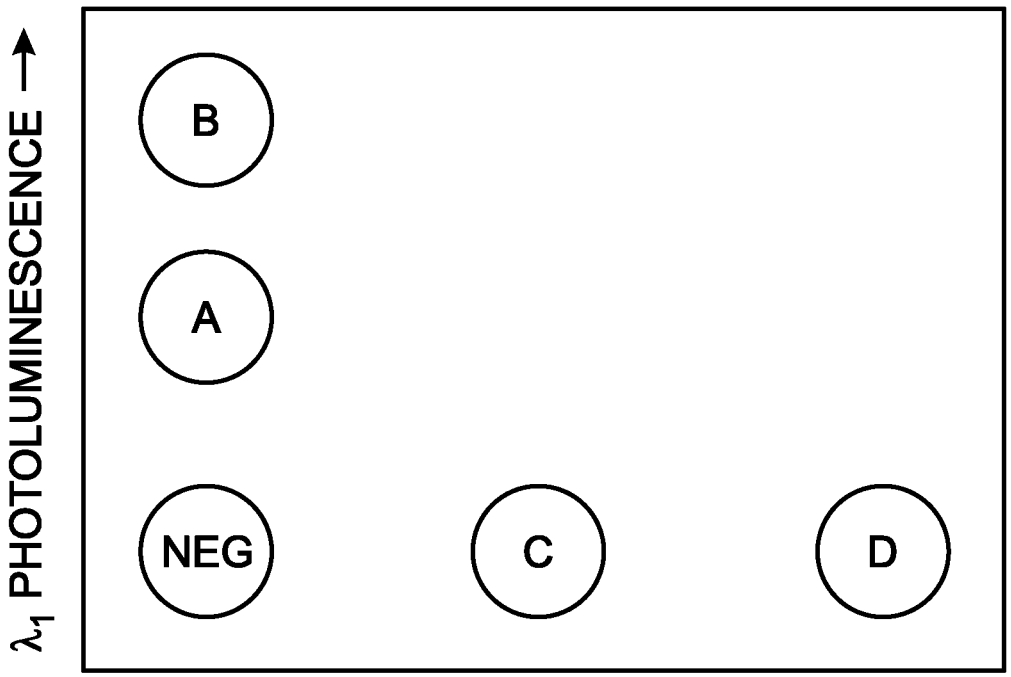
FIG. 1 is a schematic representation of photoluminescence detected in a multiplex digital assay from isolated volumes at two different wavelengths ($\lambda_1$ and $\lambda_2$) from respective photoluminescent labels, where each label reports amplification of two different targets (A and B, or C and D) at different, respective increased photoluminescence intensities relative to target-negative volumes, in accordance with aspects of the present disclosure.

The present disclosure provides methods of, and compositions for, analysis using digital amplification assays with unconventional/inverse changes in photoluminescence to indicate the presence of one or more targets. In an exemplary method, isolated volumes may be formed, only a subset of which contain a target. Each volume may include a probe having a label, a sink having a quencher and configured to hybridize with the probe to quench the label, and a separator configured to hybridize with the probe and/or the sink to block hybridization of the sink with the probe. An amplification reaction may be performed in the volumes to generate an amplicon corresponding to the target. The separator may hybridize with the amplicon, and may be extended or degraded by the amplification reaction. Photoluminescence of the label may be detected from the volumes, and the photoluminescence of target-positive volumes may be less than that of target-negative volumes.

An exemplary composition for analysis is provided. The composition may comprise a plurality of isolated volumes. Each volume may include a portion of the same sample, a probe having a photoluminescent label, a sink configured to hybridize with the probe and having a quencher for the label, and a separator. Only a subset of the volumes may contain at least one copy of a target from the sample. Each volume may contain amplification reagents to generate an amplicon corresponding to the target. The separator may be configured to block hybridization of the sink with the probe in target-negative volumes, and also may be configured to be extended or degraded preferentially in target-positive volumes by generation of the amplicon. In some embodiments, the composition may be an emulsion, with the volumes being aqueous droplets each surrounded by an immiscible carrier liquid (a continuous phase), such as oil.

The methods and compositions of the present disclosure may offer various advantages. The presence of different targets in a set of volumes may be distinguished from one another more reliably in multiplex digital assays based on differences in photoluminescence intensity. Also, the degree of multiplexing (number of different targets) may be increased, without the need for a different detector. Furthermore, assays in which the presence of two different targets are detected at the same wavelength may be more robust, because the characteristic photoluminescence intensities of volumes containing each target can be separated farther from one another, and/or offset with inverse polarity from the characteristic photoluminescence intensity of target-negative volumes.

Further aspects of the present disclosure are presented in the following sections: (I) definitions, (II) overview of photoluminescence changes in digital assays, (III) methods of sample analysis for one or more targets, (IV) exemplary methods and reagent configurations, (V) further aspects of analysis methods, (VI) compositions, and (VII) examples.

I. DEFINITIONS

Technical terms used in this disclosure have meanings that are commonly recognized by those skilled in the art. However, the following terms may be further defined as described below.

Nucleic acid oligomer—a relatively short polynucleotide (i.e., an oligonucleotide) or a relatively short polynucleotide analogue (i.e., an oligonucleotide analogue). Exemplary analogues include peptide nucleic acids, locked nucleic acids, phosphorothioates, etc. The oligomer may have an unbranched (or branched) chain of conjugated units, namely, nucleotides or nucleotide analogues, each containing a base (e.g., a nucleobase). An oligomer may, for example, contain less than about 200, 100, 75, or 50 units, where each unit is a nucleotide or nucleotide analogue. The oligomer may be chemically synthesized or biosynthesized, among others. The oligomer may be labeled with at least one label, which may be conjugated to the chain and considered part of the oligomer. The at least one label may include at least one photoluminophore and thus may be a photoluminescent label. Each label may be conjugated to the chain of the oligomer at any suitable position, including its 5'-end, 3'-end, or intermediate the 5'- and 3'-ends. The oligomer (e.g., as a separator, sink, probe, or integral sink-probe (e.g., see FIG. 9)) may have a 3'-end that is structured to prevent extension by a polymerase (also called a blocked 3'-end). For example, the oligomer may have a phosphate, ddC, inverted dT, C3 spacer, or amino group, among others, at its 3'-terminus.

Probe—a labeled nucleic acid oligomer (an oligonucleotide or analogue thereof), or an oligomeric portion thereof, including a photoluminescent label (e.g., from which photoluminescence is detected in an assay). The probe, interchangeably called a reporter, may be configured to hybridize with a sink, and optionally with a separator, in an assay, and/or may be configured to hybridize with at least a portion of an amplicon generated in the assay. In some embodiments, the probe may hybridize more stably to the separator than the sink (e.g., by forming a greater number of base pairs with the separator than with the sink). The probe may be capable of annealing with a strand of an amplicon generated in the assay. However, if the probe has a corresponding sink and separator, the temperature at which the probe anneals to the amplicon (i.e., the probe-amplicon annealing temperature) may be less than the minimum temperature at which amplification is performed, such as the annealing temperature or the extension temperature of a polymerase chain reaction. The probe-amplicon melting temperature may be at least about 2, 4, 6, 8, or 10 degrees Celsius less than the minimum temperature of the amplification reaction. This probe-amplicon melting temperature may minimize interference with the amplification reaction by the probe, and may discourage extension of the probe, if its 3' end is not blocked. Alternatively, if the probe does not have a corresponding sink and separator (e.g., the second probe in FIG. 12), the probe (e.g., a hydrolysis probe) may be configured to anneal with at least a portion of an amplicon during the amplification reaction, or the probe (e.g., a molecular beacon probe) may be configured to anneal with the amplicon only after the amplification reaction has been completed.

Sink—a labeled nucleic acid oligomer (an oligonucleotide or analogue thereof), or an oligomeric portion thereof, configured to hybridize with a probe, and optionally with a separator in an assay, and including a quencher for a photoluminescent label of the probe. The sink hybridized to the probe may position the quencher of the sink proximate to the label of the probe, such that the quencher significantly quenches photoluminescence from the photoluminophore. In some embodiments, the sink may hybridize more stably to the separator than the probe (e.g., by forming a greater number of base pairs with the separator than with the probe). In some embodiments, the probe and the sink may be part of the same molecule and may be configured to hybridize intramolecularly.

The melting temperature of a probe-sink hybrid may be above the temperature at which photoluminescence is detected in an assay, such as at least about 2, 4, 6, 8, or 10 degrees Celsius above the detection temperature. This melting temperature allows the probe-sink hybrid to be present during detection. The sink may be capable of annealing with a strand of an amplicon generated in the assay. However, the melting temperature of the sink hybridized to the amplicon (i.e., the sink-amplicon melting temperature) may be less than the minimum temperature at which amplification is performed, such as the annealing temperature or the extension temperature of a polymerase chain reaction. The sink-amplicon annealing temperature may be at least about 2, 4, 6, 8, or 10 degrees Celsius less than the minimum temperature of the amplification reaction. This sink-amplicon annealing temperature may minimize interference with the amplification reaction by the sink, and may discourage extension of the sink, if its 3' end is not blocked.

Separator—a nucleic acid oligomer (an oligonucleotide or analogue thereof) configured to hybridize with a target and/or with at least a portion of an amplicon (e.g., to a region of a strand thereof) during performance of an amplification reaction in an assay. The separator may be extended (e.g., by a polymerase or ligase) or degraded (e.g., hydrolyzed by a polymerase) by the amplification reaction, preferentially in target-positive volumes. Accordingly, the separator may function as an amplification primer, or as a hydrolysis probe that is unlabeled. The separator may be configured to hybridize with at least a portion of an amplicon and with a probe and/or sink, with hybridization to the amplicon being more stable than with the probe and/or sink (e.g., by forming a greater number of base pairs with the amplicon than the probe and/or sink). The separator may be longer than the probe and the sink (i.e., containing a greater number of nucleotides or analogues thereof).

The melting temperature of a separator hybrid (i.e., a probe-separator hybrid, sink-separator hybrid, or integral probe/sink-separator hybrid) may be above the temperature at which photoluminescence is detected in an assay, such as at least 2, 4, 6, 8, or 10 degrees Celsius above the detection temperature. This melting temperature allows the separator hybrid to be present during detection. The separator hybrid may be more stable than the probe-sink hybrid and may have a melting temperature that is at least about 1, 2, 4, 6, 8, or 10 degrees Celsius above the melting temperature of the probe-sink hybrid, such that the separator hybrid is formed preferentially.

The separator may be configured to anneal to a strand of an amplicon during the amplification reaction. Accordingly, the melting temperature of the separator-amplicon hybrid (i.e., the separator-amplicon melting temperature) may be greater than the minimum temperature at which amplification is performed, such as the annealing temperature or the extension temperature of a polymerase chain reaction. The separator-amplicon melting temperature may be at least about 2, 4, 6, 8, or 10 degrees Celsius greater than the minimum temperature of the amplification reaction. This separator-amplicon melting temperature can ensure that the separator anneals efficiently to the amplicon, to serve as an amplification primer or to be hydrolyzed by polymerase.

The separator, probe, and sink may be present at any suitable ratios in isolated volumes at the start of an amplification reaction. The separator may, for example, be about equimolar to the probe and/or sink to which it hybridizes, or may be present in molar excess over the probe and/or sink.

Photoluminophore—a label capable of emitting light (photoluminescing) in response to irradiation with excitation light. Light can be ultraviolet light, visible light, and/or infrared light. Exemplary forms of photoluminescence include fluorescence and phosphorescence, among others. Accordingly, the photoluminophore may, for example, be a fluorophore or a phosphor. Suitable photoluminophores may include a dye, such as FAM, VIC, HEX, ROX, TAMRA, JOE, Cyanine-3, or Cyanine-5 dye, or the like.

Quenching—any proximity-dependent process that results in a decrease in the photoluminescence intensity of a photoluminophore. The quenching may occur through any suitable mechanism or combination of mechanisms, including dynamic quenching (e.g., Förster Resonance Energy Transfer (FRET), Dexter electron transfer, Exciplex, etc.) or static/contact quenching, among others. The efficiency of quenching may be very sensitive to the distance between a photoluminophore and its quencher. For example, in FRET the efficiency of quenching is inversely related to the distance raised to the sixth power. Accordingly, small changes in the separation distance between the photoluminophore and quencher can produce large changes in the efficiency of quenching. The distance at which the quenching efficiency has dropped to 50% may be less than 10 nanometers.

Quencher—a label capable of quenching the photoluminescence of a photoluminophore, generally in a highly proximity-dependent manner. The quencher may be another photoluminophore, or may be a dark quencher that does not substantially emit light. Exemplary dark quenchers may include Black Hole Quenchers (e.g., BHQ0, BHQ1, BHQ2, BHQ3), ATTO quenchers, Iowa Black, QSY 7/9/21/35, etc.

Target—an analyte of interest in a sample. The target may be a nucleic acid target, and may be described as a target sequence.

Amplification—any process for making multiple copies of a nucleic acid sequence. The source of amplification may be described as an amplification template, and the product of amplification may be described as an amplicon. The target may be the amplification template, at least initially in an amplification reaction, or may be used to generate the amplification template, such as by acting as a ligation template for a ligation reaction. Generation of an amplicon in a volume corresponds to the presence of the target in the volume, although the sequence of the amplicon may be different from the sequence of the target. As amplification proceeds, the amplicon may serve as a template for generating additional copies of the amplicon. Exemplary amplification reactions include a polymerase chain reaction (PCR), a ligase chain reaction (LCR), etc.

Isolated volumes—volumes that are separate from one another. The volumes, which may be fluid volumes, interchangeably may be called partitions or compartments. A fluid substantially forming the volumes may be liquid, such as an aqueous liquid. The volumes may be separated from one another by gas (e.g., air), liquid (e.g., an immiscible carrier liquid or continuous phase), a solid (e.g., a wall(s) of a sample holder (such as a multi-well sample holder)), or a combination thereof. The volumes may be substantially the same size as one another. Exemplary volumes are droplets surrounded by a continuous carrier liquid, such as aqueous droplets encapsulated by a continuous oil phase, which may form an emulsion. The volumes may have substantially the same composition, except for stochastic variations in the number of copies of limited components, such as one or more targets. For example, the volumes may be aliquots of the same mixture.

II. OVERVIEW OF PHOTOLUMINESCENCE CHANGES IN DIGITAL ASSAYS

Figure 2:
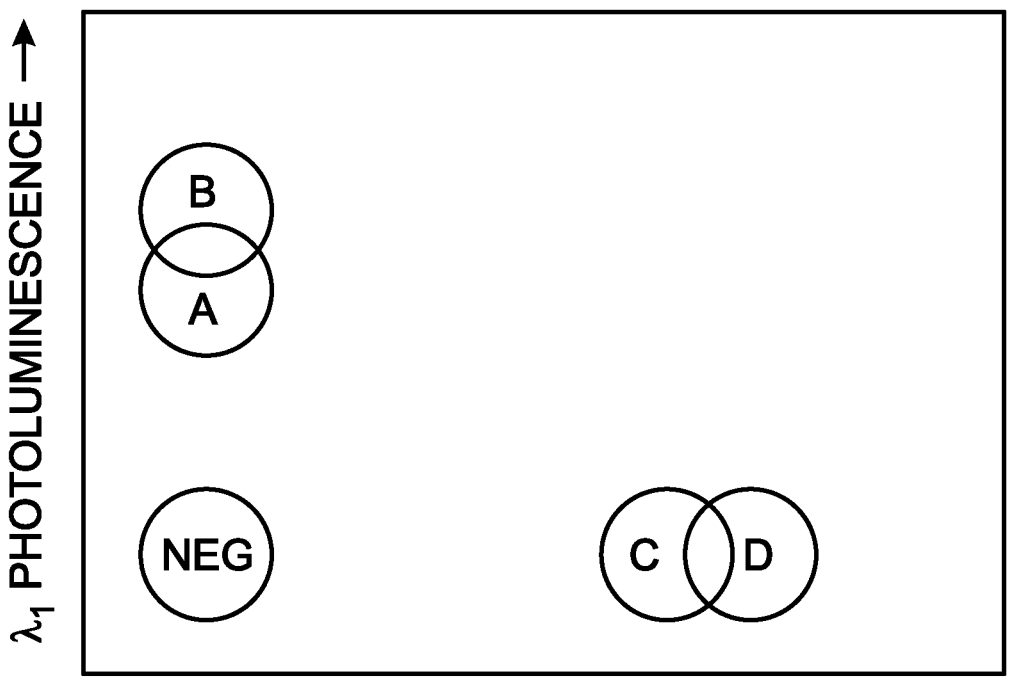
FIG. 2 is a schematic representation of photoluminescence detected as in FIG. 1, except that the increased photoluminescence intensities for the two targets at each wavelength overlap one another, which can make the assay inoperable, in accordance with aspects of the present disclosure.
Figure 3:
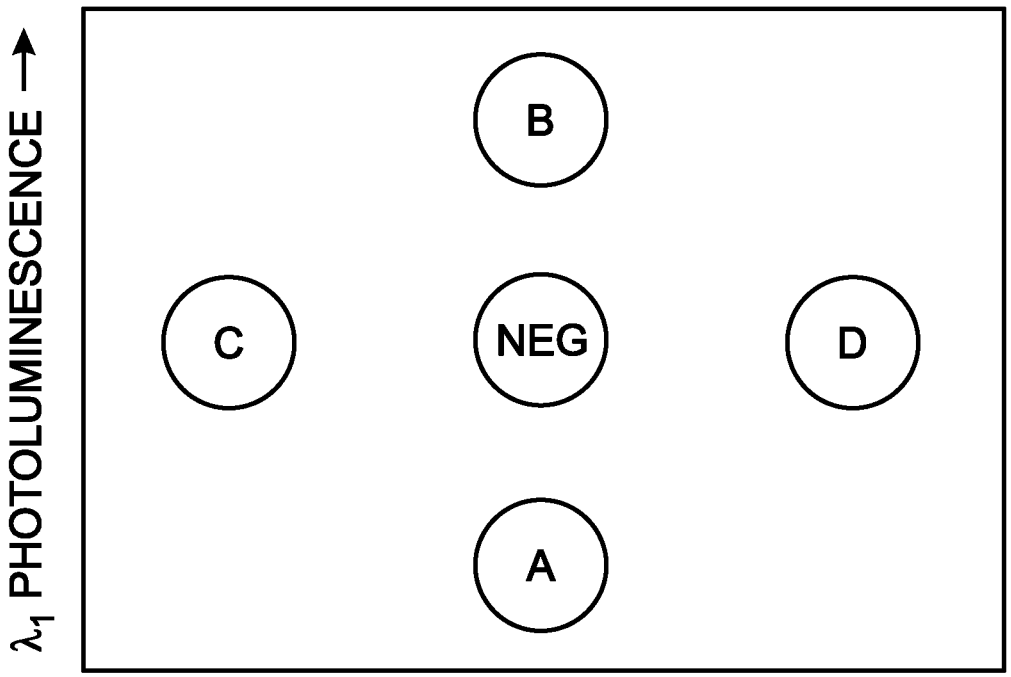
FIG. 3 is a schematic representation of photoluminescence detected in a multiplex digital assay from isolated volumes at different wavelengths ($\lambda_1$ and $\lambda_2$) respective photoluminescent labels as in FIG. 1, except that each label reports amplification of two different targets (A and B, or C and D) with inverse effects on photoluminescence intensities (relative to target-negative volumes), in accordance with aspects of the present disclosure.
Figure 4:
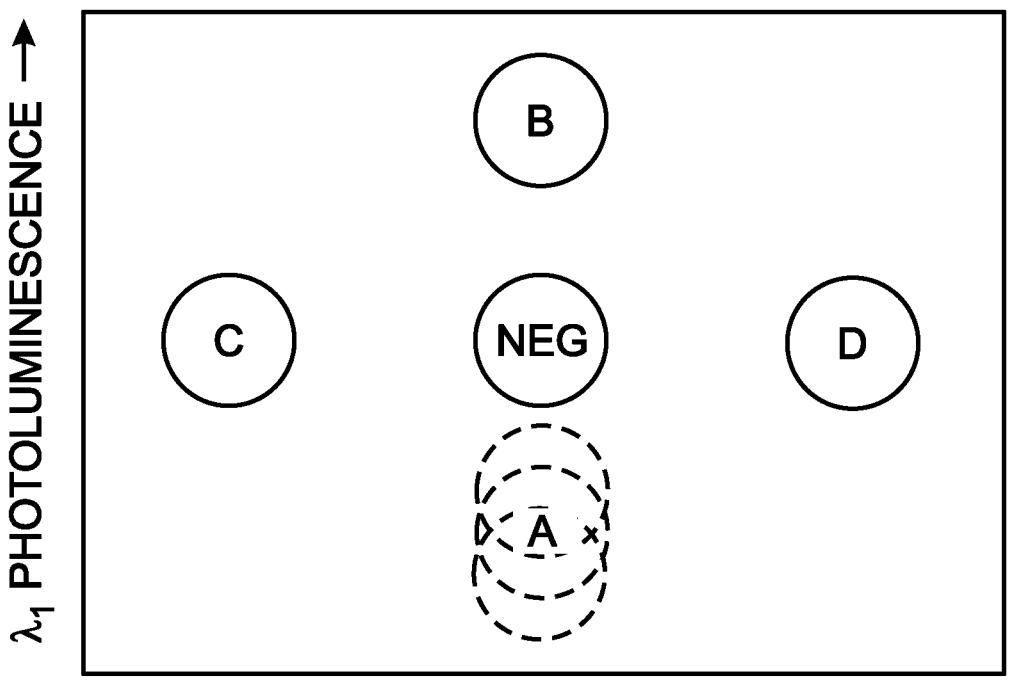
FIG. 4 is a schematic representation of photoluminescence detected as in FIG. 3, and illustrating how changes to the net-decreased photoluminescence of target-A-positive volumes can be tolerated without making the assay inoperable, in accordance with aspects of the present disclosure.

This section provides a schematic comparison of photoluminescence intensity data that may be collected in multiplex digital assays having (a) conventional changes in photoluminescence (see FIGS. 1 and 2) and (b) unconventional/inverse changes in photoluminescence (see FIGS. 3 and 4).

FIG. 1 shows a schematic plot of conventional amplification data that may be collected at two different photoluminescence detection wavelengths ($\lambda_1$ and $\lambda_2$) from isolated volumes in a multiplex digital assay. Each circle in the plot represents a cluster of the volumes plotted as points. The volumes in each circle have the same target content (i.e., containing target A, B, C, or D or no target (NEG)), and have a similar intensity of photoluminescence as one another at each of the wavelengths.

The assay may be performed as follows. A sample containing four different targets (A-D) may be divided into isolated volumes, such as droplets, such that the targets are present at "partial occupancy" in the volumes. In other words, only a subset of the volumes contain any given target, and a subset of the volumes contain none of the targets ("NEG" for negative). (To simplify the discussion, no volumes in FIG. 1 contain two or more different targets.) The targets may be amplified in the volumes in the presence of a labeled probe for each target. In FIG. 1, the respective probes for targets A and B each have a label (e.g., the same label) that fluoresces at $\lambda_1$, and the respective probes for targets C and D each have a label (e.g., the same label) that fluoresces at $\lambda_2$. The fluorescence detected from the label of the probe corresponding to each target increases when the target is amplified in a given volume. For example, volumes containing target A or target B exhibit a stronger photoluminescence at $\lambda_1$ than the target-negative volumes, and different levels of photoluminescence at $\lambda_1$ from one another. Similarly, volumes containing target C or target D exhibit a stronger photoluminescence at $\lambda_2$ than the target-negative volumes, and different levels of photoluminescence at $\lambda_2$ from one another.

FIG. 2 shows another schematic plot of conventional amplification data that may be collected at two different photoluminescence wavelengths ($\lambda_1$ and $\lambda_2$) from isolated volumes in a multiplex digital assay. The data of FIG. 2 are collected in a multiplex digital assay performed as in FIG. 1. However, due to small shifts in the characteristic photoluminescence intensities of the clusters of volumes containing each of the targets, relative to FIG. 1, the clusters for targets A and B now overlap one another, as do the clusters for targets C and D. Due to the overlap, the number of volumes containing each target can no longer be accurately determined, making the assay inoperable. Assay configurations are needed to create a greater and/or more robust separation between the intensities of different clusters of volumes in the data.

FIG. 3 shows a schematic plot of amplification data collected in a multiplex digital assay performed as in FIG. 1, except using reagent configurations for targets A and C that produce unconventional changes in photoluminescence, namely, a net decrease in photoluminescence (at $\lambda_1$ or $\lambda_2$) for volumes containing target A or C relative to target-negative volumes. Accordingly, volumes containing target A and those containing target B exhibit inverse changes in photoluminescence with respect to target-negative volumes, as do volumes containing target C and those containing target D.

FIG. 4 shows a schematic plot of amplification data collected in a multiplex digital assay performed as in FIG. 3. Exemplary shifts that may occur in the characteristic photoluminescence of target-A-containing volumes due to changes in assay conditions are shown in dashed outline. These shifts do not produce significant overlap with another cluster of volumes in the plot and thus do not render the assay inoperable. The ability of the assay to tolerate shifts in cluster positions without significant cluster overlap can be increased using the unconventional and/or inverse changes in photoluminescence of the present disclosure.

III. METHODS OF SAMPLE ANALYSIS FOR ONE OR MORE TARGETS

Figure 5:
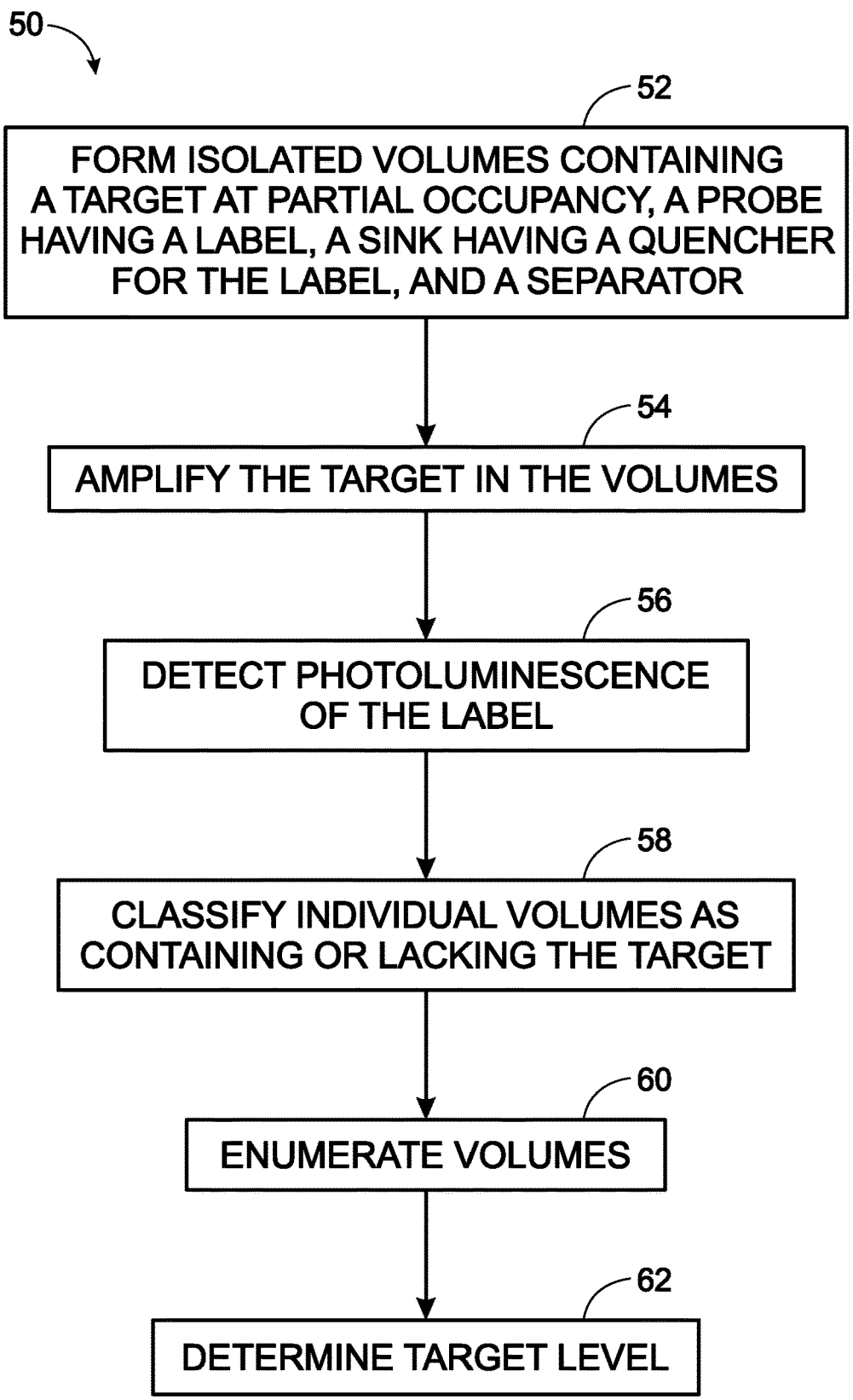
FIG. 5 is a flowchart for an exemplary method of sample analysis for a target, and utilizing isolated volumes and an unconventional change in photoluminescence to distinguish target-positive volumes from target-negative volumes, in accordance with aspects of the present disclosure.
Figure 6:
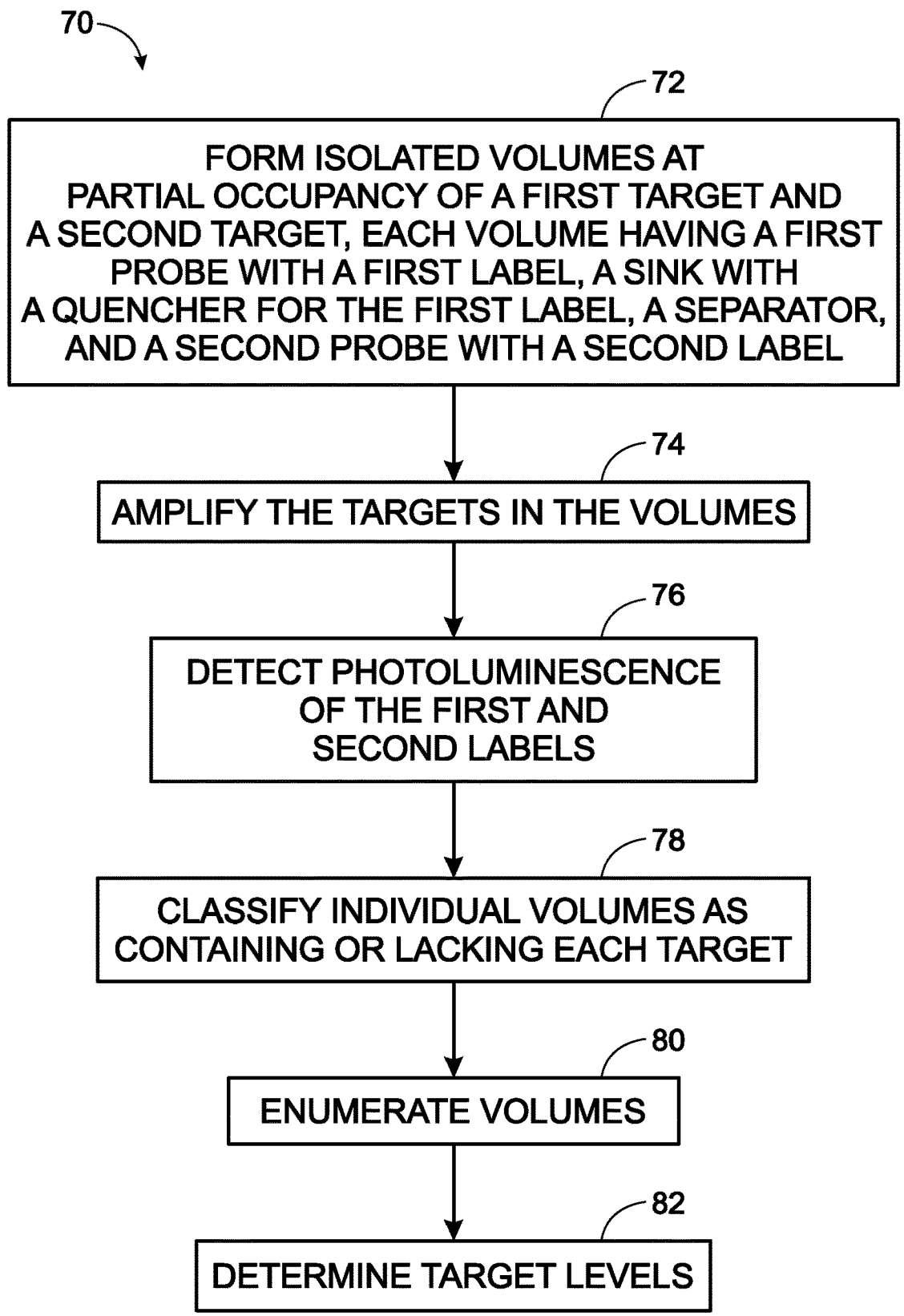
FIG. 6 is a flowchart for an exemplary method of sample analysis for a first target and a second target, and utilizing isolated volumes and inverse changes in photoluminescence to distinguish the presence of the first target from the presence of the second target in individual volumes, in accordance with aspects of the present disclosure.

This section describes exemplary methods of sample analysis for at least one target using unconventional/inverse changes in photoluminescence to detect the presence of the target(s); see FIGS. 5 and 6. The method steps described in this section may be performed in any suitable order and combination, using any of the reagent configurations described elsewhere in the present disclosure, such as in Section IV.

FIG. 5 shows a flowchart for an exemplary method 50 of sample analysis for a target. Method 50 utilizes reagents producing a net decrease in photoluminescence for target-containing volumes relative to target-lacking volumes.

Isolated volumes may be formed, indicated at 52. The volumes may contain a nucleic acid target (also called a target sequence) at partial occupancy, such that only a subset of the volumes contain at least one copy of the target. Each of the volumes may contain the same probe having a label (a photoluminophore), the same sink having a quencher for the label, the same separator, and a portion of the same sample. The volumes may be formed, at least in part, by dividing the sample into isolated volumes and/or by dividing a mixture into isolated volumes, where the mixture contains the sample, the probe, the sink, and the separator. The mixture also may contain amplification reagents, such as a polymerase, primers for generating an amplicon corresponding to the target, and nucleoside triphosphates, among others. Exemplary volumes include droplets, which may be uniform in size. Any suitable number of volumes may be formed and/or processed in the assay, such as at least about 100, 1,000, or 10,000. In some embodiments, the method may be performed with a single volume (e.g., a bulk phase), without generating a plurality of isolated volumes.

The target may be amplified in the volumes, indicated at 54. More generally, an amplicon corresponding to the target may be generated in the subset of volumes that contain at least one copy of the target. Amplification may be encouraged by heating the volumes, such as by thermal cycling (to encourage a polymerase or ligase chain reaction).

Photoluminescence of the label may be detected from the volumes, indicated at 56. Each volume may be irradiated with excitation light to excite the label, and emitted light may be detected. The photoluminescence may be detected from the volumes serially or in parallel, among others. An intensity of the photoluminescence from each volume may be detected, and may, for example, be a maximum intensity, an integrated intensity, an average intensity, or the like. Photoluminescence may be detected from any suitable number of volumes in the assay, such as at least about 100, 1,000, or 10,000.

Individual volumes may be classified as containing (target-positive) or lacking (target-negative) the target, indicated at 58. The step of classifying may be performed based on the photoluminescence detected from each volume. Due to the configuration of the probe, the sink, and the separator, target-positive volumes may emit less light than target-negative volumes. A value for the photoluminescence detected from each volume may be compared with a threshold to determine whether the volume is positive or negative for the target. If the value is below the threshold, the volume may be classified as positive, and if above the threshold, may be classified as negative.

Volumes that are positive for the target, or volumes that are negative for the target, may be enumerated, indicated at 60, to obtain a value for the number of target-positive volumes or a value for the number of target-negative volumes. A value for the total number of volumes (including target-positive and target-negative volumes) also may be enumerated.

A level of the target may be determined, indicated at 62. The level may, for example, be the average number of copies of the target per volume. The average number of copies may be calculated using the value for the number of target-positive volumes or the number of target-negative volumes, and the value for the total number of volumes, from enumerating step 60. In some embodiments, the average number may be calculated using Poisson statistics.

FIG. 6 shows a flowchart for an exemplary method 70 of sample analysis for a first target and a second target. Method 70 utilizes reagents producing a net decrease in photoluminescence, at a given wavelength or waveband, for first-target-positive volumes relative to target-negative volumes, and a net increase in photoluminescence, at the given wavelength or waveband, for second-target-containing volumes relative to target-negative volumes. In other words, the presence of the first target or the second target in respective volumes results in inverse effects on the photoluminescence detected from the volumes. The method steps of method 70, namely, steps 72, 74, 76, 78, 80, and 82, respectively correspond to steps 52, 54, 56, 58, 60, and 62 of method 50, and may be performed as described for method 50, but with the following optional differences.

Volumes may be formed, indicated at 72. The volumes may be formed as described above for step 52, where the probe is a first probe with a first label, but also include a second target at partial occupancy, and a second probe with a second label. The second probe may be configured to hybridize to an amplicon corresponding to the second target. The first label and the second label may be structurally identical to one another and/or may emit light at the same wavelength, to allow photoluminescence of the labels to be detected at the same wavelength(s). Each volume may contain primers for generation of respective amplicons corresponding to the first target and the second target. For example, each volume may contain a first pair of primers for generating the first amplicon, and a second pair of primers for generating the second amplicon.

Amplicons corresponding to the first and second targets may be generated in the volumes, indicated at 74. Amplification may be performed as described above for step 54.

Photoluminescence of the first and second labels may be detected from individual volumes, indicated at 76. The photoluminescence may be detected by the same photoluminescence detector as collective photoluminescence from both labels.

Individual volumes may be classified as containing or lacking each of the targets, indicated at 78. For example, a value for the photoluminescence detected from each volume may be compared with a first threshold and/or a second threshold. If the value is below the first threshold, the volume may be classified as positive for the first target. If the value is above the second threshold, the volume may be classified as positive for the second target. If the value is between the thresholds, the volume may be classified as negative for both targets.

Volumes may be enumerated, indicated at 80. Enumerating step 80 may be performed like enumerating step 60 described above, except that a value for the number of second-target-positive or the number of second-target-negative volumes also is obtained.

Target levels may be determined, indicated at 82. Each of the target levels may be determined as described above for step 62 of method 50.

Further aspects of methods 50 and 70 are described elsewhere herein. For example, exemplary reagent configurations for methods 50 and 70 are described in Section IV, among others. Further aspects of the steps of dividing a sample and/or forming volumes, performing an amplification reaction(s), detecting photoluminescence, classifying volumes, enumerating volumes, and determining target levels for methods 50 and 70 are described in Sections IV and V, among others.

IV. EXEMPLARY METHODS AND REAGENT CONFIGURATIONS

This section schematically illustrates and describes exemplary methods of sample analysis for at least one target using reagent configurations (i.e., compositions) that produce unconventional/inverse changes in photoluminescence; see FIGS. 7-12. The method steps of this section may be performed in any suitable order and combination, using any combination of reagents disclosed herein, and are described further elsewhere in the present disclosure, such as in Sections III and V. Further aspects of compositions associated with these methods are described elsewhere herein, such as in Section VI.

Figure 7:
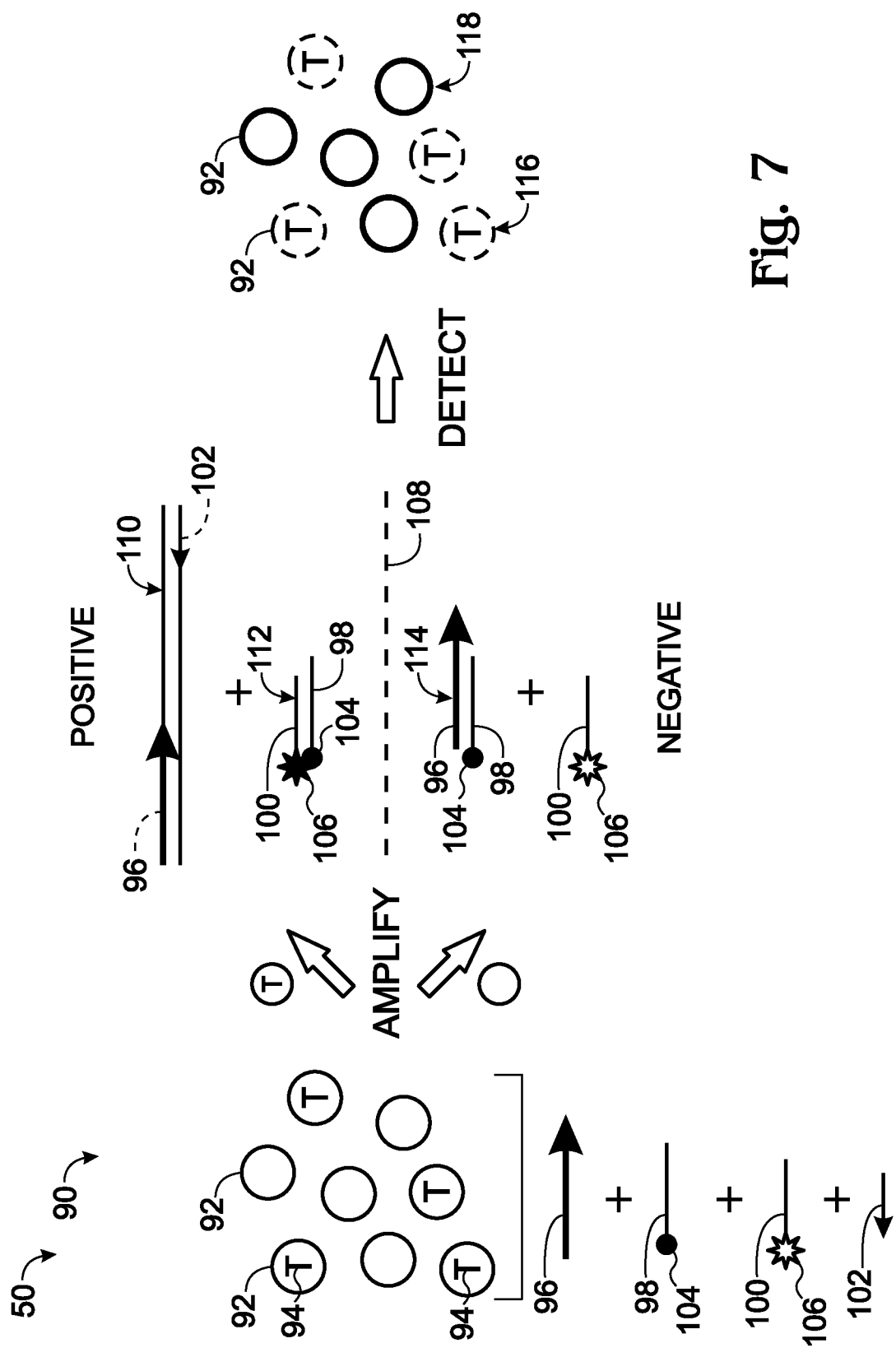
FIG. 7 is a schematic representation of an exemplary digital amplification assay utilizing a net decrease in photoluminescence to indicate target presence, and performed with isolated volumes each containing a separator that at least reduces or substantially eliminates the ability of a sink to quench the photoluminescence detectable from a label of a probe, but preferentially in amplification-negative volumes lacking the target, because the separator functions as a primer for amplification of the target in target-positive volumes, such that the label produces stronger photoluminescence in target-negative volumes than target-positive volumes, in accordance with aspects of the present disclosure.

FIG. 7 shows aspects of an exemplary digital amplification assay 90 utilizing a net decrease in photoluminescence to indicate target presence. Isolated volumes 92 are illustrated on the left before target amplification, with only a subset of the volumes containing at least one copy of a nucleic acid target 94 ("T"). As illustrated under the set of volumes, each volume 92 may contain a separator 96, a sink 98, a probe 100, and a primer 102, each of which may include or be a nucleic acid oligomer (or an oligomeric portion thereof). In the depicted embodiment, separator 96 and primer 102 are configured as respective forward and reverse primers for amplification of target 94, with the 3'-ends of the separator and primer identified by arrowheads. Each volume also may include a polymerase (e.g., a heat-stable polymerase) and dNTPs or NTPs for addition to the 3'-ends of the primers as they are being extended.

Each of sink 98 and probe 100 may be labeled with suitable moieties. Sink 98 may have at least one quencher 104 (also called a quencher moiety) attached to the chain of a nucleic acid oligomer. Probe 100 has at least one photoluminophore 106 (also called a photoluminophore moiety) attached to the chain of a nucleic acid oligomer. The quencher is capable of quenching light emission from the photoluminophore, when they are sufficiently proximate to one another (e.g., when the sink is hybridized to the probe). Each quencher moiety and/or photoluminophore moiety may be chemically bonded, such as covalently bonded, to the corresponding chain of the nucleic acid oligomer.

An amplification reaction may be performed in volumes 92. The result of amplification is contrasted schematically for target-positive volumes, represented above a dashed line 108, and for target-negative volumes, represented below the dashed line. The amplification reaction may generate an amplicon 110 corresponding to target 94 only in target-positive volumes. Each of separator 96 and primer 102 forms one of the complementary strands of the amplicon by primer extension, which reduces the amount of the separator available for hybridization with sink 98 (and/or probe 100 (also see FIGS. 9 and 12)).

Sink 98 is sufficiently complementary to separator 96 and probe 100 for hybridization to each during performance of the assay, such as after amplification has been completed and before photoluminescence is detected. A probe-sink hybrid 112 is formed by base pairing of sink 98 and probe 100 with one another (above dashed line 108). A separator-sink hybrid 114 is formed by base pairing of separator 96 and sink 98 with one another (below dashed line 108). However, separator-sink hybrid 114 is more stable, which allows the separator to outcompete probe 100 for hybridization with sink 98 in target-negative volumes. The amount of separator 96 is reduced in target-positive volumes by primer extension, which allows formation of probe-sink hybrid 112 in those volumes.

The ability of photoluminophore 106 of probe 100 to emit light after amplification is determined by the degree of hybridization of the probe with sink 98. In target-positive volumes, a greater percentage of probe 100 is quenched by sink 98, due to formation of probe-sink hybrid 112. Photoluminophore 106 is filled in hybrid 112 above dashed line 108, to indicate that the photoluminophore is preferentially quenched in target-positive volumes. Accordingly, a lower photoluminescence intensity is detected from target-positive volumes, indicated schematically on the right side of FIG. 7 at 116 and by a dashed line bounding each target-positive volume. In target-negative volumes, a lesser percentage of probe 100 is quenched by sink 98, due to the greater amount of separator 96 available for forming the more stable separator-sink hybrid 114. Photoluminophore 106 is unfilled below dashed line 108, to indicate that the photoluminophore emits more light in target-negative volumes, shown schematically on the right side of FIG. 7 at 118 and by a solid line bounding each target-negative volume.

The methods and reagent configurations shown in FIGS. 8-12 generally are illustrated using the same logic and conventions as those described above for FIG. 7. Accordingly, the discussion below of FIGS. 8-12 focuses primarily on how the following methods and reagent configurations differ from those of FIG. 7.

Figure 8:
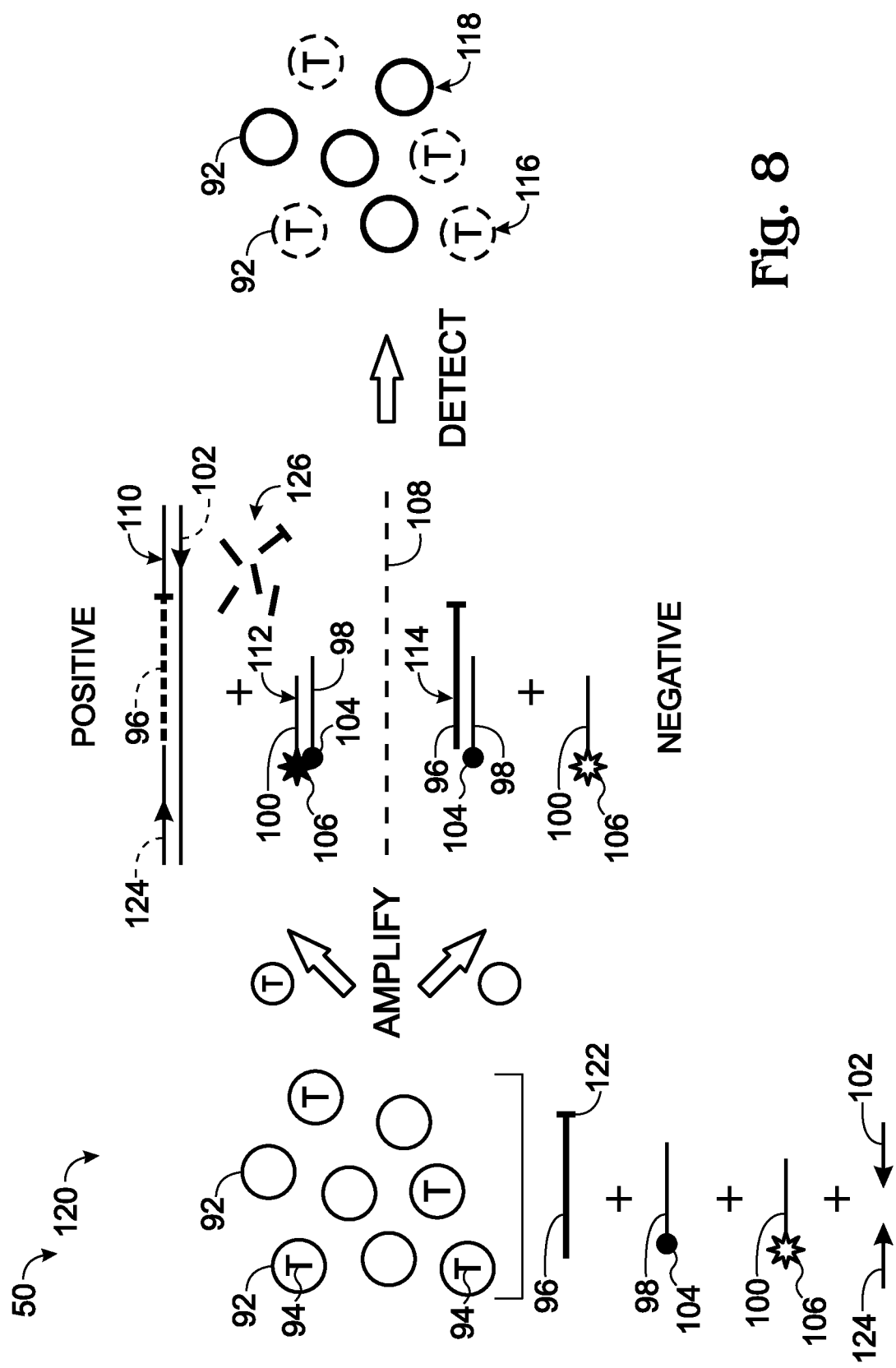
FIG. 8 is another schematic representation of an exemplary digital amplification assay utilizing a net decrease in photoluminescence to indicate target presence as in FIG. 7, except that the separator has a blocked 3'-end and is degraded selectively in target-positive volumes, in accordance with aspects of the present disclosure.

FIG. 8 shows aspects of another exemplary digital amplification assay 120 utilizing a net decrease in photoluminescence to indicate target presence. The method illustrated in FIG. 8 utilizes a separator 96 having a blocked 3'-end, indicated at 122, which prevents the separator from being extended by polymerase during amplification. The separator thus does not act as an amplification primer; a separate forward primer 124 serves this role instead. Separator 96 hybridizes to a region of target 94 and/or an amplicon 110 generated by amplification, as shown by a dashed representation of the separator within the amplicon. Extension of one of the primers by polymerase (e.g., forward primer 124 in the depicted embodiment) during the amplification reaction may cause at least a molar fraction of the separator to be hydrolyzed, indicated at 126, selectively in target-positive volumes (above dashed line 108). The resulting decrease in the amount of separator in target-positive volumes allows more probe-sink hybrid 112, and less separator-sink hybrid 114, to be present in target-positive volumes, relative to target-negative volumes, when photoluminescence is detected. The effect on the intensity of photoluminescence is the same as in FIG. 7, namely, a net decrease for target-positive volumes compared to target-negative volumes, indicated at 116 and 118 on the right side of FIG. 8.

Figure 9:
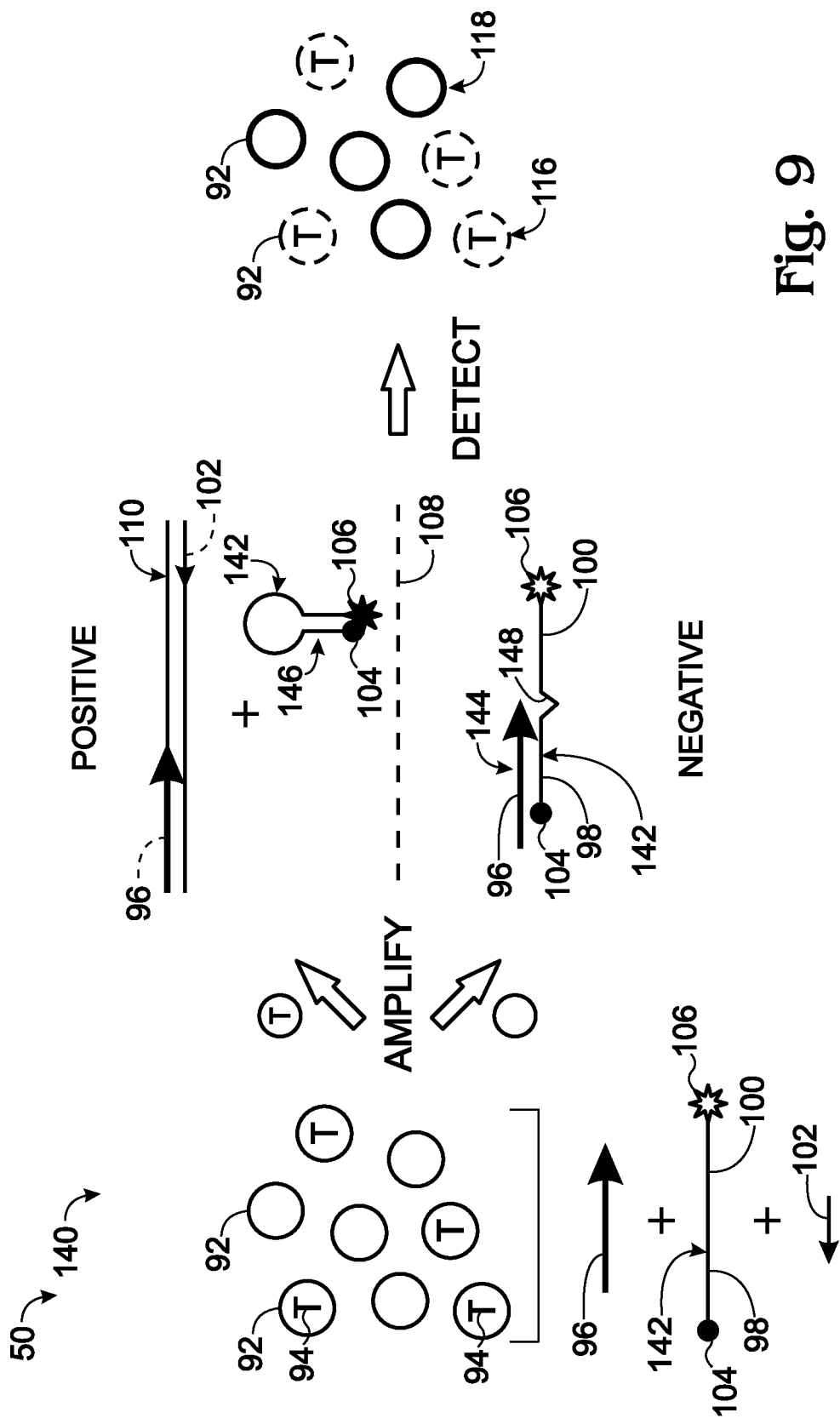
FIG. 9 is yet another schematic representation of an exemplary digital amplification assay utilizing a net decrease in photoluminescence to indicate target presence as in FIG. 7, except that the probe and the sink are covalently linked to one another, in accordance with aspects of the present disclosure.

FIG. 9 shows aspects of yet another exemplary digital amplification assay 140 utilizing a net decrease in photoluminescence to indicate target presence. The method illustrated in FIG. 9 utilizes a self-quenching reporter 142 to provide both a sink 98 with a quencher 104, and a probe 100 with a photoluminophore 106 (compare with separate sink 98 and probe 100 molecules of FIG. 7). In other words, the probe and the sink may be covalently linked to one another within the same molecule, and may hybridize with one another intramolecularly to create a stem-loop structure, also called a hairpin. A spacer sequence is disposed between the probe sequence and the sink sequence of the reporter. The spacer sequence forms the loop, and the probe sequence and the sink sequence hybridize with one another to form the stem of the stem-loop structure.

Separator 96 may be configured to hybridize with reporter 142, to form a separator-reporter hybrid 144 having an increased distance between quencher 104 and photoluminophore 106, relative to an intramolecular probe-sink hybrid 146 of reporter 142. Separator-reporter hybrid 144 may block intramolecular hybridization of reporter 142, and may be more stable than intramolecular probe-sink hybrid 146. The decrease in the amount of separator 96 in target-positive volumes, caused by primer extension in the depicted embodiment (or hydrolysis (see FIG. 8)), allows more intramolecular probe-sink hybrid 146, and less separator-reporter hybrid 144, to be present in target-positive volumes, relative to target-negative volumes, when photoluminescence is detected. The effect on the intensity of photoluminescence is the same as in FIG. 7, namely, a net decrease for target-positive volumes compared to target-negative volumes, indicated at 116 and 118 on the right side of FIG. 9.

The 3'-end of separator 96 may be unable to base pair with reporter 142, shown at 148. This lack of complementary may prevent extension of separator 96 by polymerase with reporter 142 as a template. Alternatively, the 3'-end of separator 96 may be blocked, as in FIG. 8, and the separator may be hydrolyzed selectively in target-positive volumes.

Separator 96 may be configured to hybridize with any suitable portion(s) of reporter 142. The separator may hybridize with a sequence of sink 98, probe 100, a spacer sequence between the sink and the probe, or any combination thereof.

Figure 10:
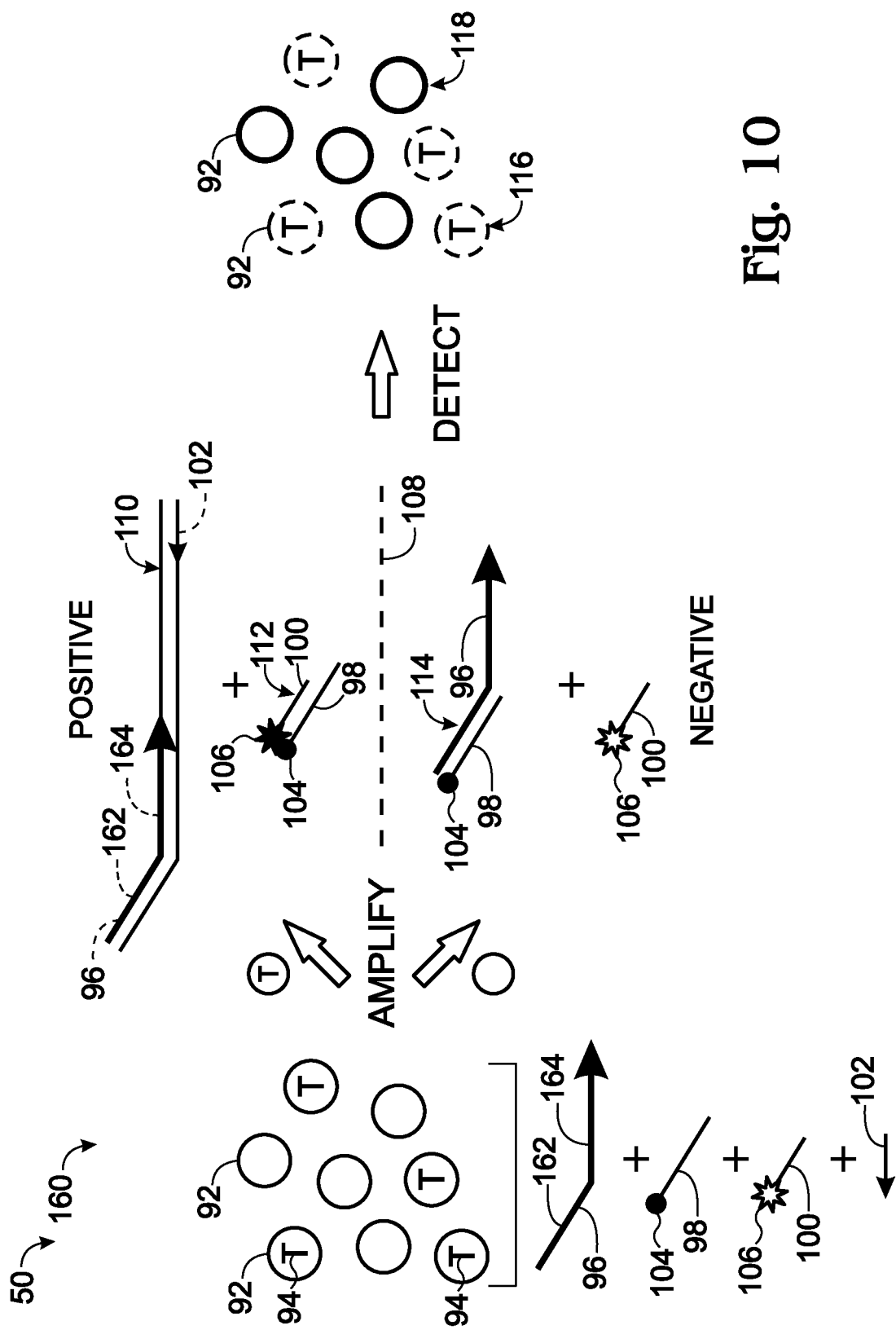
FIG. 10 is still another schematic representation of an exemplary digital amplification assay utilizing a net decrease in photoluminescence to indicate target presence as in FIG. 7, except that the separator has a 5' tail for hybridization with the sink (or probe), optionally permitting the same "universal" sink and "universal" probe to be used with different target-specific separators (e.g., having the same 5' tail), in accordance with aspects of the present disclosure.

FIG. 10 shows aspects of still another exemplary digital amplification assay 160 utilizing a net decrease in photoluminescence to indicate target presence. The method illustrated in FIG. 10 utilizes a separator 96 having a 5'-tail 162 that does not hybridize with target 94 or amplicon 110, and a 3'-sequence 164 that does hybridize with the target and amplicon. The separator serves as a forward primer during amplification. Amplicon 110 thus may contain the sequence of 5'-tail 162 on one strand and its complement on the other strand.

A sink 98 hybridizes with a probe 100 to form a probe-sink hybrid 112, and hybridizes with 5'-tail 162 to form a separator-sink hybrid 114. The decrease in the amount of separator 96 caused by amplification in target-positive volumes allows more probe-sink hybrid 112, and less separator-sink hybrid 114, to be present in target-positive volumes, relative to target-negative volumes, when photoluminescence is detected. The effect on the intensity of photoluminescence is the same as in FIG. 7, namely, a net decrease for target-positive volumes compared to target-negative volumes, indicated at 116 and 118 on the right side of FIG. 10. In other embodiments, probe 100 may hybridize with 5'-tail 162 of the separator.

A separator having a 5'-tail permits the same "universal" sink and "universal" probe to be used with different target-specific separators. Each of the target-specific separators may have a 5'-tail for hybridization to the universal sink (or universal probe (see FIG. 11)), but not to the target or amplicon, and a 3'-sequence that hybridizes with the target and amplicon.

Figure 11:
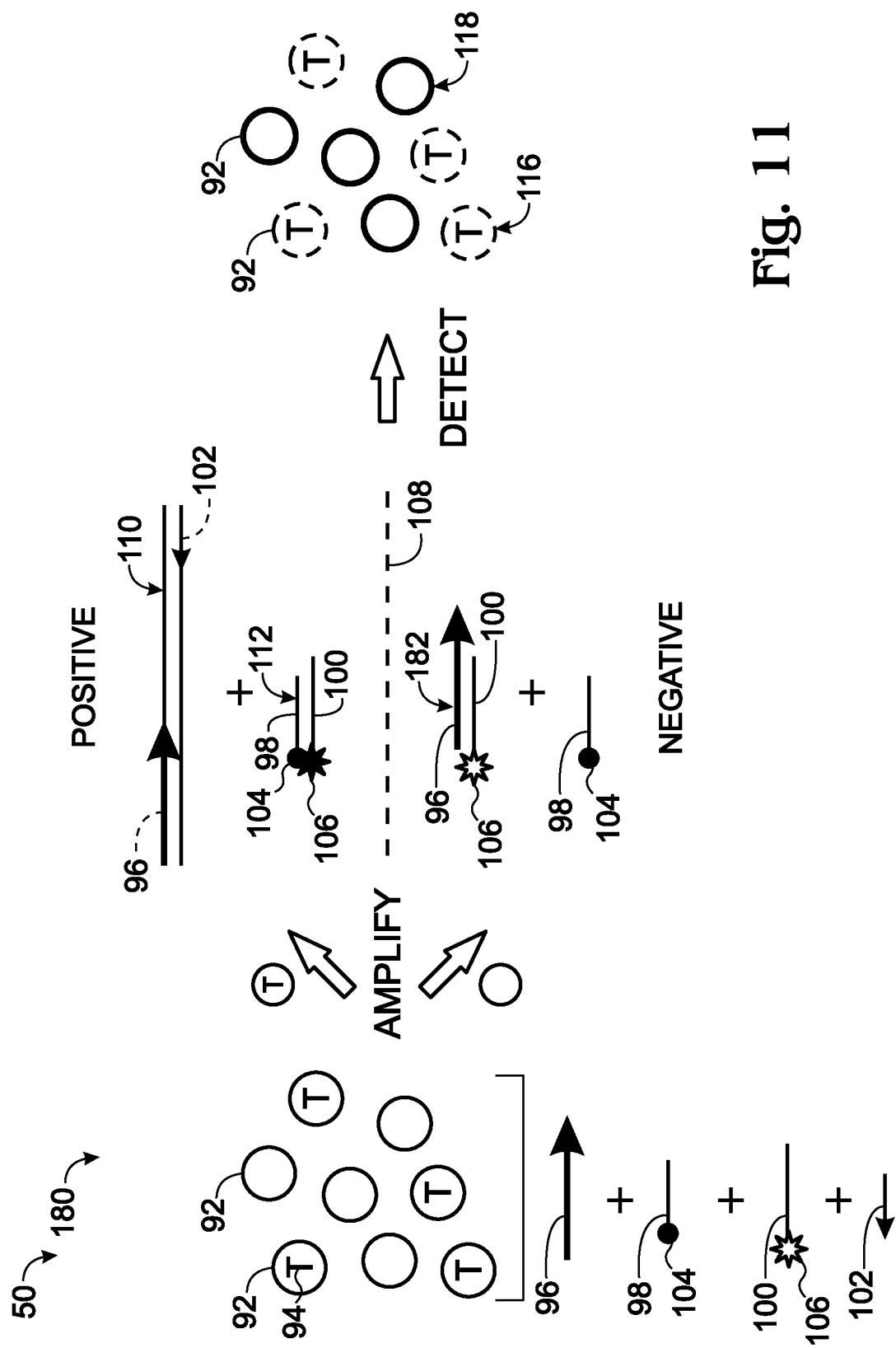
FIG. 11 is yet still another schematic representation of an exemplary digital amplification assay utilizing a net decrease in photoluminescence to indicate target presence as in FIG. 7, except that the separator hybridizes with the probe instead of the sink, in accordance with aspects of the present disclosure.

FIG. 11 shows aspects of still yet another exemplary amplification assay 180 utilizing a net decrease in photoluminescence to indicate target presence. The assay is performed as in FIG. 7, except that separator 96 hybridizes with probe 100, to form a separator-probe hybrid 182. The decrease in the amount of separator 96 in target-positive volumes, by primer extension as depicted or by hydrolysis (see FIG. 8), allows more probe-sink hybrid 112, and less separator-probe hybrid 182, to be present in target-positive volumes, relative to target-negative volumes, when photoluminescence is detected. The effect on the intensity of photoluminescence is the same as in FIG. 7, namely, a net decrease for target-positive volumes compared to target-negative volumes, indicated at 116 and 118 on the right side of FIG. 11.

Figure 12:
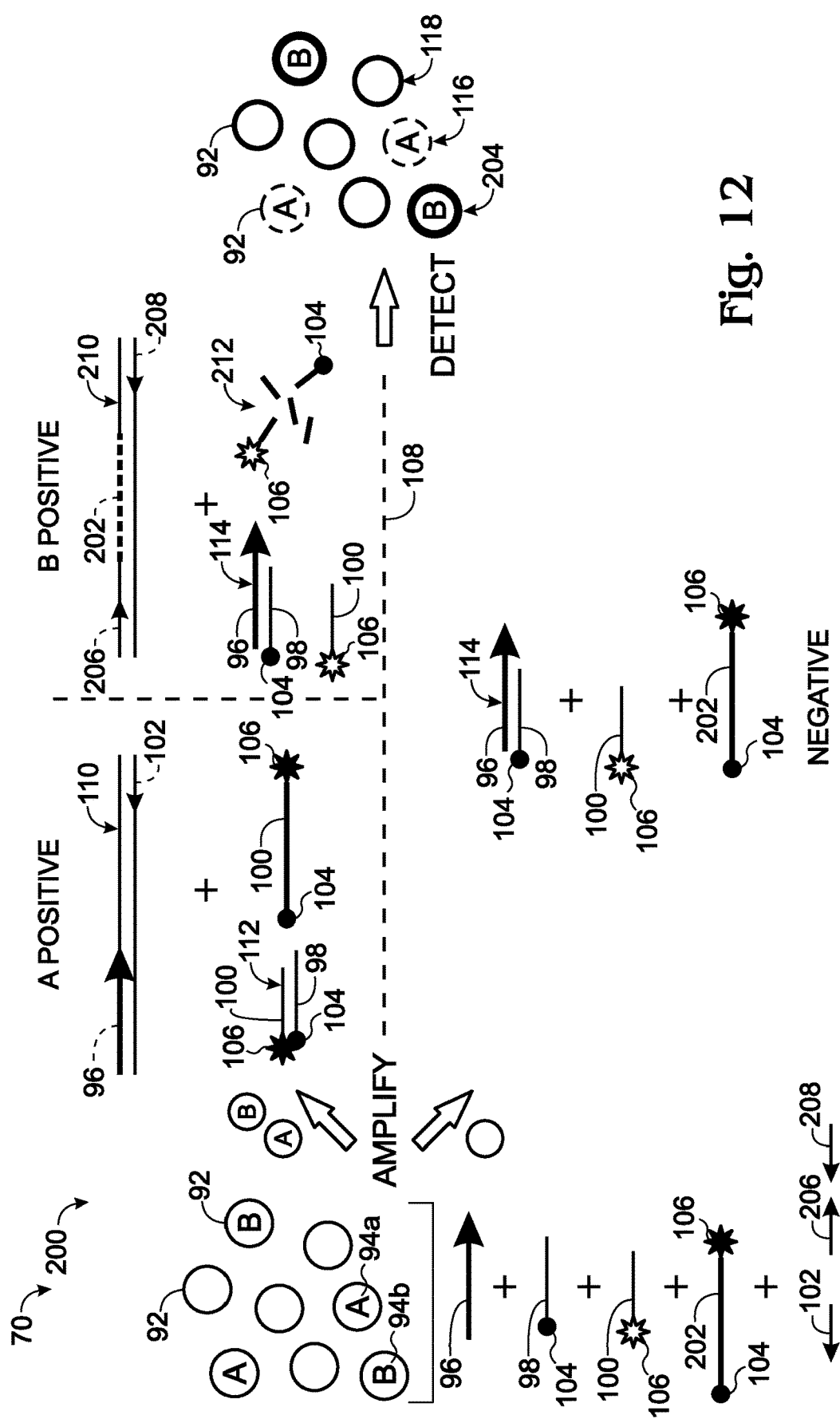
FIG. 12 is a schematic representation of an exemplary digital amplification assay for a first target and a second target that utilizes inverse changes in photoluminescence detected from the same label to indicate target presence, where the presence of the first target produces a net decrease in photoluminescence as in FIG. 7, and the presence of the second target produces a net increase in photoluminescence, in accordance with aspects of the present disclosure.

FIG. 12 shows an exemplary multiplex amplification assay 200 according to method 70. The method quantifies a first target 94a ("A") and a second target 94b ("B"), and utilizes inverse changes in photoluminescence detected from the same label (photoluminophore 106) of different probes 100, 202 to indicate the presence of each target 94a, 94b. The presence of first target 94a produces a net decrease in photoluminescence relative to no target, as in FIG. 7, indicated at 116 and 118 on the right side of FIG. 12. In other embodiments, the net decrease may be produced by any of the assay configurations of FIGS. 8-11, instead of that of FIG. 7. The presence of second target 94b produces a net increase in photoluminescence relative to no target, indicated at 204 on the right side of FIG. 12.

Volumes 92 may be formed that contain targets 94a, 94b at partial occupancy, meaning that only a subset of the volumes contain at least one copy of first target 94a, and only a subset of the volumes contain at least one copy of second target 94b. Each volume also may contain the set of reagents described above for FIG. 7 (or any of FIGS. 8-11), including a separator 96, a sink 98, a probe 100, and a reverse primer 102 (or a pair of primers for amplification of first target 94a if the separator is configured to be hydrolyzed rather than extended).

Each volume further may comprise reagents for detecting the presence of second target 94b, namely, probe 202 and amplification primers 206, 208 to generate an amplicon 210 corresponding to second target 94b. Probe 202 may include a quencher 104 and a photoluminophore 106 that is quenched by the quencher in a proximity-dependent manner. In other embodiments, respective different photoluminophores that emit light at the same detection wavelength and/or within the same detection waveband may label probe 100 and probe 202. In the depicted embodiment, probe 202 is a hydrolysis probe that is blocked at its 3'-end and complementary to amplicon 210. At least a molar fraction of probe 202 is degraded during amplification, indicated at 212 and by a dashed form of probe 202 shown in amplicon 210. Probe 202 is degraded selectively in volumes containing second target 94b, which unlinks quencher 104 and photoluminophore 106 of the probe from one another. In other embodiments, probe 202 may be a molecular beacon probe, a displacement probe, or any other of the probes described elsewhere herein, such as in Section V.

V. FURTHER ASPECTS OF ANALYSIS METHODS

This section describes further exemplary aspects of the methods of Sections III and IV, among others. The steps described in this section may be performed in any suitable order and combination, with any of the assay configurations, components, and features described elsewhere herein, such as in Sections I-IV.

Reaction mixture preparation. A reaction mixture may be prepared. The reaction mixture may be an amplification mixture configured to support amplification of each target and thus may contain all of the reagents necessary for amplification of an amplicon corresponding to each target provided by a sample that is present in the reaction mixture. The reagents, which are described in more detail below, may, for example, include dNTPs and/or NTPs, a polymerase (e.g., an RNA polymerase or a DNA polymerase, either of which may or may not be heat stable), a ligase, buffer, water, surfactant, and/or the like. The reagents also may include a pair of primers and a labeled probe for each target. For at least one target, the probe may have a photoluminescent label, and the reaction mixture also may include a sink having a quencher for the label, and a separator.

Polynucleotides in the reaction mixture provide the target(s) and may have any suitable structure and characteristics. Each target may be at least predominantly single-stranded or at least predominantly double-stranded, among others, in the reaction mixture before performing the amplification reaction(s). Each target may, for example, be at least predominantly DNA (e.g., genomic DNA, mitochondrial DNA, or cDNA), at least predominantly RNA (e.g., genomic RNA, transcribed RNA, messenger RNA, tRNA, ribosomal RNA, etc.), a combination thereof (e.g., a DNA-RNA hybrid), or the like. Molecules providing each target may be uniform in length (e.g., formed by restriction enzyme digestion or used as full-length), or may vary in size (e.g., formed by random fragmentation, such as shearing, digestion with a nonspecific nuclease, etc.). The targets may be provided by a sample that contains a complex mixture of different nucleic acids (different polynucleotides), with the target(s) being a minor species. The sample may include nucleic acid, and the nucleic acid may be composed substantially of genomic DNA, mitochondrial DNA, genomic RNA, total RNA, nuclear RNA, cytoplasmic RNA, messenger RNA, or any combination thereof, among others.

The primers may include a forward primer and a reverse primer for generation of each amplicon. The forward primer and the reverse primer may define the ends of the amplicon. Any of the primers disclosed herein may be oligonucleotides of any suitable length, such as at least 10, 15, or 20 nucleotides, among others.

In some embodiments, formation of the reaction mixture may include combining the sample with reagents for amplification and one or more reporters (also called signaling agents) for reporting whether or not amplification occurred. Reagents for amplification may include any combination of one or more primers for synthesis an amplicon corresponding to each target, dNTPs and/or NTPs, at least one enzyme (e.g., a polymerase, a ligase, a reverse transcriptase, a restriction enzyme, or a combination thereof, each of which may or may not be heat-stable), and/or the like.

The reporters may have any suitable structure and characteristics. The reporter for one of the targets may be a probe that hybridizes with at least a portion of an amplicon (e.g., see probe 202 of FIG. 12). The probe may include an oligonucleotide and a photoluminophore chemically bonded (e.g., covalently bonded) to the oligonucleotide, to label the oligonucleotide. The probe also may include a quencher that is chemically bonded (e.g., covalently bonded) to the oligonucleotide. The probe may be capable of hybridizing with at least a portion (e.g., a strand) of the corresponding amplicon. The probe may or may not also function as an amplification primer that is extended to form at least part of the amplicon in the assay. Exemplary labeled probes include TaqMan® probes, Scorpion® probes/primers, Eclipse® probes, Amplifluor® probes, molecular beacon probes, Lux® primers, proximity-dependent pairs of hybridization probes that exhibit FRET when bound adjacent one another on an amplicon, QZyme® primers, or the like.

Volume formation. A sample containing each target may be divided into isolated volumes. The sample may be divided by separating the reaction mixture described above into isolated volumes, or the sample may be divided before it is combined with all of the reagents of the assay, among others.

The volumes when formed may contain each target at "partial occupancy," which means that a subset (one or more) of the volumes contains no copies of the target and the rest of volumes contain at least one copy of the target. For example, another subset (one or more) of the volumes may contain a single copy (only one copy) of the target, and, optionally, yet another subset (one or more) of the volumes (e.g., the rest of the volumes) may contain two or more copies of the target. The term "partial occupancy" is not restricted to the case where there is no more than one copy of the target in any volume. Accordingly, volumes containing the target at partial occupancy may, for example, contain an average of more than, or less than, about one copy, two copies, or three copies, among others, of the target per volume when the volumes are formed. Copies of the target may have a random distribution among the volumes, which may be described as a Poisson distribution.

Volume formation may involve disposing any suitable portion including up to all of the sample/reaction mixture in the volumes. Each volume is spatially isolated from every other volume. The volumes may be isolated from one another by a fluid/liquid phase, such as a continuous phase of an emulsion or air, by a solid phase, such as at least one wall of a container, or a combination thereof, among others. In some embodiments, the volumes may be droplets disposed in a continuous carrier liquid, such that the droplets and the continuous phase collectively form an emulsion.

The volumes may be formed by any suitable procedure, in any suitable manner, and with any suitable properties. For example, the volumes may be formed with a fluid dispenser, such as a pipette, with at least one droplet generator having an orifice and/or a channel intersection at which droplets are created, by agitation of the sample/reaction mixture (e.g., shaking, stirring, sonication, etc.), and/or the like. Accordingly, the volumes may be formed serially, in parallel, or in batch. The volumes may have any suitable size(s). The volumes may have the same size or may have different sizes. Exemplary volumes having the same size are monodisperse droplets. Exemplary sizes for the volumes include less than about 100, 10 or 1 µL, less than about 100, 10, or 1 nL, or less than about 100, 10, or 1 pL, among others.

Volumes competent for amplification of each target may be formed directly from a bulk phase containing copies of the target, or may be formed in multiple steps. In some cases, the step of forming volumes may include dividing a bulk phase into isolated fluid volumes (such as droplets) containing the target at partial occupancy. These fluid volumes may be the volumes used for the assay or may contribute to the volumes. For example, these fluid volumes may be a first set of fluid volumes, and the step of forming volumes may include combining individual fluid volumes of the first set with individual fluid volumes of a second set. The second set may include one or more reagents for amplification of one or more of the targets, such as at least one primer for amplification of at least one of the targets, a probe, or the like. The step of combining may include fusing fluid volumes of the first set individually with fluid volumes of the second set, such as fusing droplets containing the target with droplets containing primers for amplification.

Amplification. An amplification reaction may be performed in the volumes. An amplicon corresponding to each target may be generated at least predominantly or exclusively in volumes containing at least one copy of the target.

Amplification may or may not be performed isothermally. In some cases, amplification in the volumes may be encouraged by thermal cycling, namely, subjecting the volumes to multiple cycles of heating and cooling. The volumes may be incubated at a denaturation temperature (e.g., greater than about 90 degrees Celsius), an annealing temperature (e.g., about 50-75 degrees Celsius), and/or an extension temperature (e.g., about 60 to 80 degrees Celsius), for one or a plurality of cycles. In some examples, the volumes may be thermally cycled to promote a polymerase chain reaction and/or ligase chain reaction. Exemplary isothermal amplification approaches that may be suitable include nucleic acid sequence-based amplification, transcription-mediated amplification, multiple-displacement amplification, strand-displacement amplification, rolling-circle amplification, loop-mediated amplification of DNA, helicase-dependent amplification, and single-primer amplification, among others.

Photoluminescence detection. Photoluminescence may be detected from volumes at any suitable time. For example, the photoluminescence may be detected before amplification has been completed (e.g., within an exponential phase or linear phase of amplification, for a kinetic assay) or after amplification is substantially complete (e.g., in a plateau phase of amplification, for an endpoint assay).

Light emitted by a photoluminophore of a probe(s) may be detected. Detection of light may be described as collection of amplification data. The data may be collected by detecting light emitted from individual intact volumes. The light may be emitted in response to irradiation of the volumes with excitation light. The data may be collected for emission of light from the volumes in one spectral region (one optical channel), a pair of different spectral regions (two optical channels) (e.g., one for each label), or the like. The different spectral regions are defined by different wavelengths and/or wavebands relative to one another.

An optical channel may represent a particular detection regime with which emitted light is generated and detected. The detection regime may be characterized by a wavelength/waveband (i.e., a wavelength regime) for detection of emitted light. If pulsed excitation light is used in the detection regime to induce light emission, the detection regime may be characterized by a wavelength or waveband for illumination with excitation light and/or a time interval during which light emission is detected with respect to each light pulse. Accordingly, optical channels that are different from each other may differ with respect to the wavelength/waveband of excitation light, with respect to the wavelength/waveband of emitted light that is detected, and/or with respect to the time interval during which emitted light is detected relative to each pulse of excitation light, among others.

Data may be collected from a plurality of the volumes under any suitable conditions. All of the data may be collected at about the same temperature from the plurality of volumes, such as at a temperature that is below a melting temperature of each amplicon, below about 50, 40, or 30 degrees Celsius, below a melting temperature of a probe-sink hybrid (and/or a separator-probe hybrid, a separator-sink hybrid, and/or a separator-reporter hybrid) in the volumes, and/or below the minimum temperature at which the amplification reaction was performed.

Obtaining signal values. The photoluminescence detected may be processed to obtain at least one signal value for each volume. For example, a photoluminescence signal may be parsed to identify a signal portion corresponding to each volume. Then, a signal value for the volume may be obtained from the signal portion, such as by integrating over the signal portion, taking a maximum or average value of the signal over the signal portion, or the like. In any event, each volume may be assigned a signal value for each label and/or optical channel.

Classification of volumes. Each volume may be classified as being positive or negative for each target based on the at least one signal value for the volume. The signal value may be compared to one or more thresholds for classification, as described elsewhere herein.

Enumeration of volumes. A respective number of volumes positive (or negative) for each target may be enumerated, and a total number volumes may be enumerated, as described elsewhere herein.

Calculation of target level(s). A level of each target may be calculated. The calculation, for a given target, may be based on a first value for the number of volumes that are positive (or that are negative) for the target, and, optionally, a second value for the total number of volumes (target-positive volumes plus target-negative volumes).

The level may be an absolute or relative level of the target. The absolute level may, for example, be a number of molecules/copies of the target, or a concentration of the target (e.g., per volume), among others. The relative level may, for example, be a relative copy number of the target with respect to a reference target, among others. The relative level alternatively may be a relative quantity of the target expressed per genome, per mass of nucleic acid (e.g., per mass of genomic DNA), or the like.

The level may represent the level of the target that was present before amplification. Determination of levels may (or may not) be based on each target having a Poisson distribution among the volumes. Each level may, for example, be a value representing the total number of volumes positive (or negative) for the target, or a concentration value, such as a value representing the average number of copies of the target per volume, among others. The data further may be used (e.g., directly and/or as concentration data) to estimate copy number (CN) and copy number variation (CNV), or any other property of the sample, using any suitable algorithms.

A level (e.g., concentration) of each target may be determined with Poisson statistics. The concentration may be expressed with respect to the volumes and/or with respect to a sample providing the target. The concentration of the target in the volumes may be calculated from the fraction of target-positive volumes (or, equivalently, the fraction of target-negative volumes) by assuming that copies of the target (before amplification) have a Poisson distribution among the volumes. With this assumption, the fraction $f(k)$ of volumes having k copies of the target is given by the following equation:

$$f(k) = \frac{\lambda^k}{k!} e^{-\lambda} \qquad (1)$$

Here, $\lambda$ is the concentration of the target in the volumes, expressed as the average number of target copies per volume (before amplification). Simplified Poisson equations may be derived from the more general equation above and may be used to determine target concentration from the fraction of target-positive volumes. An exemplary Poisson equation that may be used is as follows:

$$\lambda = -\ln\left(1 - \frac{N_+}{N_{tot}}\right) \quad (2)$$

where $N_+$ is the number of volumes (i.e., the volume count) positive for a given target, and where $N_{tot}$ is the total number of volumes (target-positive plus target-negative). $N_{tot}$ is equal to a sum of (a) $N_+$ for the target and (b) the number of volumes negative for the target, or $N_-$. $N_+/N_{tot}$ (or $N_+/(N_+ + N_-)$) is equal to $f_+$, which is the fraction of volumes positive for the template (i.e., $f_+ = f(1) + f(2) + f(3) + \ldots$) (see Equation 1), and which is a measured estimate of the probability of a volume having at least one copy of the template. Another exemplary Poisson equation that may be used is as follows:

$$\lambda = -\ln\left(\frac{N_-}{N_{tot}}\right) \quad (3)$$

where $N_-$ and $N_{tot}$ are as defined above. $N_-/N_{tot}$ is equal to $f_-$, the fraction of negative volumes (or $1-f_+$), and is a measured estimate of the probability of a volume having no copies of the target, and $\lambda$ is the target concentration as described above.

Equations 2 and 3 above can be rearranged to produce the following:

$$\lambda = \ln(N_{tot}) - \ln(N_{tot} - N_+) \quad (4)$$

$$\lambda = \ln(N_{tot}) - \ln(N_-) \quad (5)$$

The concentration of each target in an assay can, for example, be determined with any of Equations 2 to 5, using values (i.e., volume counts) obtained for $N_{tot}$ and $N_-$ or, equivalently, $N_+$, for each target. In some cases, the value used for $N_{tot}$ (the total volume count) may be the same for each target. In other cases, the value used for $N_{tot}$ may vary, such as if some of the populations are excluded from the total count due to population overlap. In some embodiments, $N_{tot}$ may be equivalent to a combination of all populations, namely, a sum of the volume counts for all populations identified.

In some embodiments, the level of a target may be obtained directly from the positive fraction, without use of Poisson statistics. In particular, the positive fraction and the concentration (copies per volume) converge as the concentration decreases. For example, with a positive fraction of 0.1, the concentration is determined with Equation 2 to be about 0.105, a difference of only 5%; with a positive fraction of 0.01, the concentration is determined to be about 0.01005, a ten-fold smaller difference of only 0.5%. However, the use of Poisson statistics can provide a more accurate estimate of concentration, particularly with a relatively higher positive fraction, because Poisson statistics takes into account the occurrence of multiple copies of the same target in the same volumes.

Further aspects of reaction mixture preparation, volume formation, amplification, detection, signal processing, enumerating volumes, and calculating levels/quantities, among others, that may be suitable for the system of the present disclosure are described elsewhere in the present disclosure, and in the references identified in the Cross-References, which are incorporated herein by reference.

VI. COMPOSITIONS

This section describes exemplary compositions of the present disclosure. Each composition may include at least one volume or a plurality of isolated volumes. If the composition comprises a plurality of volumes, each volume may include a portion of the same sample, a probe having a photoluminescent label, a sink configured to hybridize with the probe such that the sink quenches the label, and a separator configured to block hybridization of the sink with the probe. If the composition comprises a plurality of volumes, only a subset of the volumes may contain at least one copy of a target from the sample. Each volume may contain amplification reagents to generate an amplicon corresponding to the target, as described elsewhere herein. The separator may be configured to block hybridization of the sink with the probe preferentially in target-negative volumes, and may be configured to be extended or degraded preferentially in target-containing volumes by generation of the amplicon. The volumes may be the same size as one another.

In some embodiments, the volumes may be isolated from one another by an immiscible liquid that encapsulates each volume. Accordingly, the composition may include an emulsion comprising the volumes and the immiscible liquid.

In some embodiments, the probe may be a first probe, and each of the volumes may contain a second probe having a photoluminescent label. The respective labels of the first and second probes may be identical to one another and/or may have overlapping emission spectra.

VII. EXAMPLES

The following examples describe selected aspects and embodiments of digital amplification assays with unconventional/inverse changes in photoluminescence. These aspects and embodiments are intended for illustration and should not limit the entire scope of the present disclosure.

Example 1. Assay Data

Figure 13:
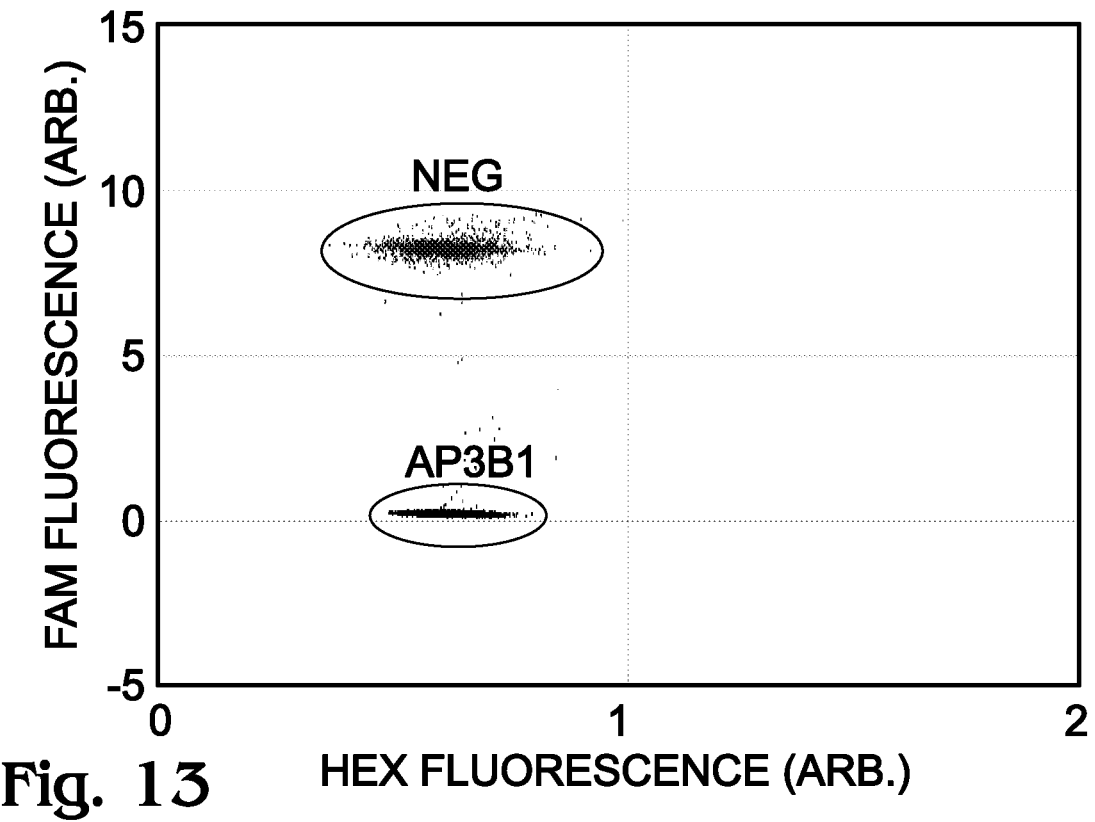
FIG. 13 is a scatter plot of amplification data collected in a singleplex digital assay performed generally as in FIG. 7, with the isolated volumes being droplets encapsulated by an immiscible carrier liquid, and showing a decrease in FAM fluorescence intensity for droplets containing an AP3B1 target relative to target-negative droplets.
Figure 14:
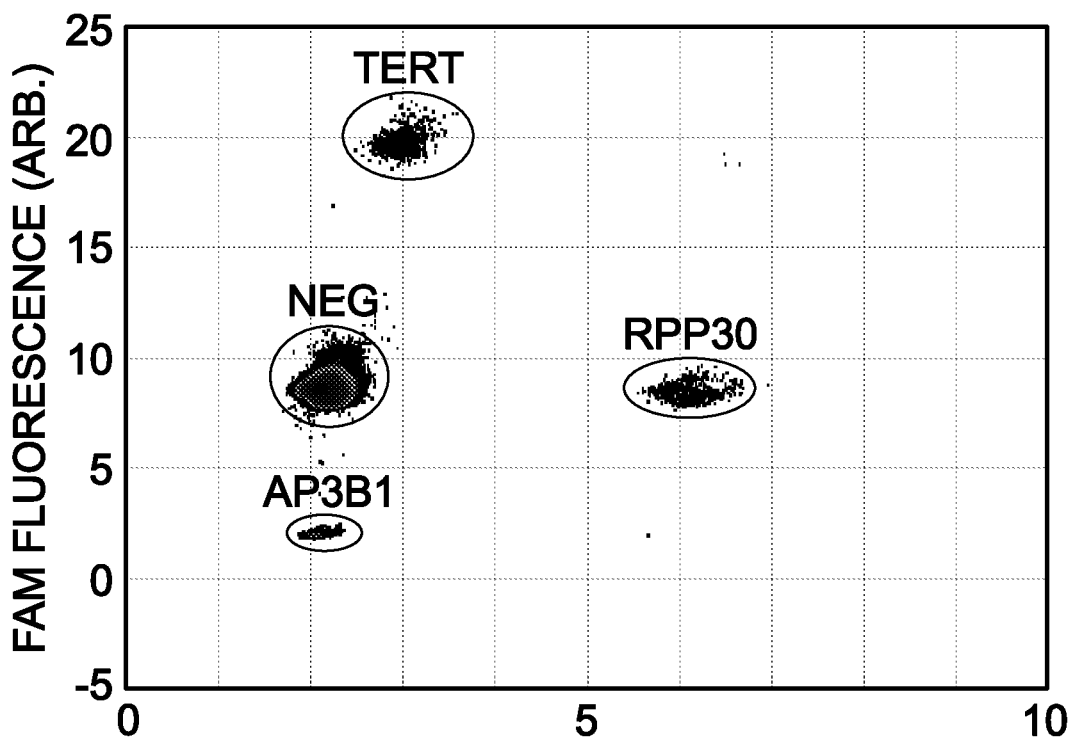
FIG. 14 is a scatter plot of amplification data collected in a multiplex digital assay performed generally as in FIG. 13, except with the addition of primers and probes for TERT and RPP30 targets, and showing the TERT and RPP30 target-containing droplets each having an increased fluorescence intensity relative to target-negative droplets.

This example presents exemplary assay data collected from a singleplex amplification assay and a multiplex amplification assay each including a separator for an AP3B1 target, and a corresponding probe and sink; see FIGS. 13 and 14 (also see FIGS. 7 and 12).

FIG. 13 shows a plot of fluorescence detected from droplets formed and processed generally as shown in FIG. 7. Each droplet contained a pair of primers to amplify a sequence from the AP3B1 gene, a probe labeled with FAM dye, and a sink configured to hybridize to the probe and labeled with a quencher for the FAM dye. One of the primers was also a separator configured to hybridize to the sink to prevent probe-sink hybridization that quenches fluorescence of the FAM dye.

Fluorescence was detected in two different spectral regions representing FAM dye fluorescence and HEX dye fluorescence. However, HEX dye was not present in the assay; the spread of values for HEX fluorescence was unrelated to the presence/absence of the target and facilitated plotting the data for easier visualization.

Each droplet is represented as a single point in FIG. 13 and is located within the plot according to the FAM and HEX fluorescence intensities detected. The droplets form two clusters: an AP3B1-negative (NEG) cluster having stronger FAM fluorescence, and an AP3B1-positive cluster having weaker FAM fluorescence.

FIG. 14 shows a plot of fluorescence detected from droplets formed and processed generally as shown in FIG. 12, except also assayed for a third target. Each droplet contained AP3B1 primers, TERT primers, and RPP30 primers. Amplification of an AP3B1 sequence was reported by a decrease in FAM fluorescence as in FIG. 13, with AP3B1 corresponding to target A in FIG. 12. Amplification of a TERT sequence also was reported by FAM fluorescence using a FAM-labeled hydrolysis probe (as for target B in FIG. 12). Amplification of an RPP30 sequence was reported by HEX fluorescence using a HEX-labeled hydrolysis probe. Clusters of droplets positive for each target (TERT, AP3B1, or RPP30) are labeled in FIG. 14, as is a negative cluster (NEG) containing none of the targets. The TERT cluster and AP3B1 cluster exhibit inverse changes in FAM fluorescence, when each is compared to the negative cluster.

Example 2. Selected Embodiments

This example describes selected embodiments of the present disclosure presented as a series of indexed paragraphs.

Paragraph 1. A method of analysis, the method comprising: (A) forming isolated volumes each including a portion of the same sample, wherein each volume also includes (i) a probe having a label, (ii) a sink having a quencher and configured to hybridize with the probe to quench the label, and (iii) a separator configured to hybridize with the probe and/or the sink to block hybridization of the sink with the probe, and wherein only a subset of the volumes contain at least one copy of a target from the sample; (B) performing an amplification reaction in the volumes to generate an amplicon corresponding to the target, wherein the separator hybridizes with the amplicon, and wherein the separator is extended or degraded in target-positive volumes by the amplification reaction; and (C) detecting photoluminescence of the label from the volumes, wherein the photoluminescence of target-positive volumes is less than that of target-negative volumes.

Paragraph 2. The method of paragraph 1, wherein the separator hybridizes with the sink to block hybridization of the sink with the probe.

Paragraph 3. The method of paragraph 1, wherein the separator hybridizes with the probe to block hybridization of the sink with the probe.

Paragraph 4. The method of any of paragraphs 1 to 3, wherein the separator hybridized with the probe and/or sink has more base pairs than the sink hybridized with the probe.

Paragraph 5. The method of any of paragraphs 1 to 4, wherein the separator forms more base pairs with the amplicon than with the probe and/or sink.

Paragraph 6. The method of any of paragraphs 1 to 5, wherein the separator hybridized with the amplicon has a higher melting temperature than the separator hybridized with the probe and/or sink.

Paragraph 7. The method of any of paragraphs 1 to 6, wherein the probe and the sink are not covalently linked to one another.

Paragraph 8. The method of any of paragraphs 1 to 6, wherein the probe and the sink are provided by the same molecule.

Paragraph 9. The method of paragraph 8, wherein the separator is configured to block intramolecular hybridization of the sink with the probe.

Paragraph 10. The method of paragraph 9, wherein the separator hybridizes with a probe sequence, a sink sequence, and/or with a spacer sequence between the probe sequence and the sink sequence.

Paragraph 11. The method of any of paragraphs 1 to 10, wherein the probe and/or the sink is structured to prevent 3'-extension of the probe and/or the sink during the step of performing an amplification reaction.

Paragraph 12. The method of paragraph 11, wherein at least one of the probe and the sink includes a 3'-terminal phosphate.

Paragraph 13. The method of any of paragraphs 1 to 12, wherein the separator is extended as an amplification primer in the step of performing an amplification reaction.

Paragraph 14. The method of any of paragraphs 1 to 12, wherein the separator is hydrolyzed by the amplification reaction.

Paragraph 15. The method of paragraph 14, wherein the separator is structured to prevent 3'-extension of the separator during the step of performing an amplification reaction.

Paragraph 16. The method of any of paragraphs 1 to 15, wherein the separator has a 5'-tail that does not hybridize with the target and a 3'-sequence that hybridizes with the target, and wherein the probe or the sink hybridizes with the 5'-tail but not the 3'-sequence of the separator.

Paragraph 17. The method of any of paragraphs 1 to 16, wherein the step of forming includes a step of forming each volume as an aliquot of the same mixture.

Paragraph 18. The method of any of paragraphs 1 to 17, wherein each volume is a droplet, and wherein the step of forming includes a step of generating droplets.

Paragraph 19. The method of any of paragraphs 1 to 18, wherein the step of performing an amplification reaction includes a step of thermally cycling the volumes to promote a polymerase chain reaction.

Paragraph 20. The method of any of paragraphs 1 to 19, further comprising a step of irradiating the volumes with excitation light to induce the photoluminescence.

Paragraph 21. The method of any of paragraphs 1 to 20, further comprising a step of classifying individual volumes as positive or negative for the target based on the photoluminescence detected.

Paragraph 22. The method of paragraph 21, wherein the step of classifying includes a step of comparing a value of an intensity of the photoluminescence detected for a given volume with at last one threshold.

Paragraph 23. The method of paragraph 22, wherein the intensity is an integrated intensity for the given volume.

Paragraph 24. The method of any of paragraphs 1 to 23, further comprising a step of enumerating target-positive volumes or target-negative volumes.

Paragraph 25. The method of paragraph 24, further comprising a step of determining a level of the target based on a value obtained in the step of enumerating.

Paragraph 26. The method of paragraph 25, wherein the step of determining a level uses a first value for the number of target-positive volumes or target-negative volumes and a second value for a total number of volumes.

Paragraph 27. The method of any of paragraphs 1 to 26, wherein the target is a first target and the probe is a first probe, wherein only a subset of the volumes contain a second target, wherein each of the volumes contains a second probe for the second target, and wherein the photoluminescence is higher for volumes containing the second target than for volumes containing neither the first target nor the second target.

Paragraph 28. A method of analysis, the method comprising: (A) forming isolated volumes each including a probe, a sink, and a separator, the probe having a label and the sink having a quencher for the label, wherein only a subset of the volumes contain at least one copy of a target; (B) amplifying the target in the volumes; (C) detecting photoluminescence of the label from individual volumes; and (D) classifying individual volumes as containing or lacking the target using the photoluminescence; wherein the separator blocks hybridization of the sink with the probe in target-lacking volumes, and wherein the separator is extended or degraded in target-containing volumes by target amplification, such that the photoluminescence of the target-containing volumes is less than that of the target-lacking volumes.

Paragraph 29. A composition for analysis, comprising: a plurality of isolated volumes, each volume including a portion of the same sample, a probe having a photoluminescent label, a sink configured to hybridize with the probe and having a quencher for the label, and a separator; wherein only a subset of the volumes contain at least one copy of a target from the sample, wherein each volume contains amplification reagents to generate an amplicon corresponding to the target, wherein the separator is configured to block hybridization of the sink with the probe in target-negative volumes, and wherein the separator is configured to be extended or degraded in target-containing volumes by generation of the amplicon.

Paragraph 30. The composition of paragraph 29, further comprising an emulsion including the volumes as droplets and also including an immiscible carrier liquid surrounding the droplets.

The disclosure set forth above may encompass multiple distinct inventions with independent utility. Although each of these inventions has been disclosed in its preferred form(s), the specific embodiments thereof as disclosed and illustrated herein are not to be considered in a limiting sense, because numerous variations are possible. The subject matter of the inventions includes all novel and nonobvious combinations and subcombinations of the various elements, features, functions, and/or properties disclosed herein. The following claims particularly point out certain combinations and subcombinations regarded as novel and nonobvious. Inventions embodied in other combinations and subcombinations of features, functions, elements, and/or properties may be claimed in applications claiming priority from this or a related application. Such claims, whether directed to a different invention or to the same invention, and whether broader, narrower, equal, or different in scope to the original claims, also are regarded as included within the subject matter of the inventions of the present disclosure. Further, ordinal indicators, such as first, second, or third, for identified elements are used to distinguish between the elements, and do not indicate a particular position or order of such elements, unless otherwise specifically stated. Finally, the present disclosure incorporates material by reference. If any ambiguity or conflict in the meaning of a term results from this incorporation by reference, the literal contents of the application govern construction of the term.

We claim:

1. A method of analysis, the method comprising:
   forming isolated volumes each including a portion of the same sample, wherein each volume also includes (i) a probe having a label, (ii) a sink having a quencher and configured to hybridize with the probe to quench the label, and (iii) a separator configured to hybridize with the probe and/or the sink to directly block hybridization of the sink with the probe, and wherein only a subset of the volumes contain at least one copy of a target from the sample;
   performing an amplification reaction in the volumes to generate an amplicon corresponding to the target, wherein the separator hybridizes with the amplicon, and wherein the separator is degraded in target-positive volumes by the amplification reaction; and
   detecting photoluminescence of the label from the volumes, wherein the photoluminescence of target-positive volumes is less than that of target-negative volumes.

2. The method of claim 1, wherein the separator hybridizes with the sink to block hybridization of the sink with the probe.

3. The method of claim 2, wherein the separator also hybridizes with the probe to block hybridization of the sink with the probe.

4. The method of claim 1, wherein the separator hybridized with the probe and/or sink has more base pairs than the sink hybridized with the probe.

5. The method of claim 1, wherein the separator forms more base pairs with the amplicon than with the probe and/or sink.

6. The method of claim 1, wherein the separator hybridized with the amplicon has a higher melting temperature than the separator hybridized with the probe and/or sink.

7. The method of claim 1, wherein the probe and the sink are not covalently linked to one another.

8. The method of claim 1, wherein the probe and the sink are provided by the same molecule, and wherein the separator is configured to block intramolecular hybridization of the sink with the probe.

9. The method of claim 8, wherein the separator hybridizes with a probe sequence, a sink sequence, and/or with a spacer sequence between the probe sequence and the sink sequence.

10. The method of claim 1, wherein the probe and/or the sink is structured to prevent 3'-extension of the probe and/or the sink during the step of performing an amplification reaction.

11. The method of claim 1, wherein the separator has a 5'-tail that does not hybridize with the target and a 3'-sequence that hybridizes with the target, and wherein the probe or the sink hybridizes with the 5'-tail but not the 3'-sequence of the separator.

12. The method of claim 1, further comprising a step of classifying individual volumes as positive or negative for the target based on the photoluminescence detected.

13. The method of claim 12, wherein the step of classifying includes a step of comparing a value of an intensity of the photoluminescence detected for a given volume with at least one threshold.

14. The method of claim 1, further comprising a step of enumerating target-positive volumes or target-negative volumes.

15. The method of claim 14, further comprising a step of determining a level of the target based on a value obtained in the step of enumerating.

16. The method of claim 15, wherein the step of determining a level uses a first value for the number of target-positive volumes or target-negative volumes and a second value for a total number of volumes.

17. The method of claim 1, wherein the target is a first target and the probe is a first probe, wherein only a subset of the volumes contain a second target, wherein each of the volumes contains a second probe for the second target, and wherein the photoluminescence is higher for volumes containing the second target than for volumes containing neither the first target nor the second target.

18. A composition for analysis, comprising:
a plurality of isolated volumes, each volume including a portion of the same sample, a probe having a photoluminescent label, a sink configured to hybridize with the probe and having a quencher for the label, and a separator; wherein only a subset of the volumes contain at least one copy of a target from the sample, wherein each volume contains amplification reagents to generate an amplicon corresponding to the target, wherein the separator is configured to directly block hybridization of the sink with the probe in target-negative volumes, and wherein the separator is configured to be degraded in target-containing volumes by generation of the amplicon.

19. A method of analysis, the method comprising:
forming isolated volumes each including a portion of the same sample, wherein each volume also includes (i) a probe having a label, (ii) a sink having a quencher and configured to hybridize with the probe to quench the label, and (iii) an undegraded separator configured to hybridize with the probe and/or the sink to block hybridization of the sink with the probe, and wherein only a subset of the volumes contains at least one copy of a target from the sample;
performing an amplification reaction in the volumes to generate an amplicon corresponding to the target, wherein the undegraded separator hybridizes with the amplicon, wherein the undegraded separator is degraded in target-positive volumes by the amplification reaction, and wherein the degraded separator does not block hybridization of the sink with the probe; and
detecting photoluminescence of the label from the volumes, wherein the photoluminescence of target-positive volumes is less than that of target-negative volumes.

* * * * *